United States Patent
Koul et al.

(10) Patent No.: US 12,117,435 B2
(45) Date of Patent: Oct. 15, 2024

(54) PORTABLE ELECTROCHEMICAL-SENSOR SYSTEM FOR ANALYZING USER HEALTH CONDITIONS AND METHOD THEREOF

(71) Applicant: Cardiai Technologies Ltd., Calgary (CA)

(72) Inventors: Raman Koul, Calgary (CA); Razieh Salahandish, Calgary (CA); Gang Wang, Calgary (CA); Sumrita Bhat, Calgary (CA); Nikhil Suresh Vastarey, Calgary (CA); Anmol Singh Kapoor, Calgary (CA)

(73) Assignee: CARDIAI TECHNOLOGIES LTD., Calgary (CA)

( * ) Notice: Subject to any disclaimer, the term of this patent is extended or adjusted under 35 U.S.C. 154(b) by 853 days.

(21) Appl. No.: 17/261,476

(22) PCT Filed: Nov. 4, 2019

(86) PCT No.: PCT/CA2019/051567
§ 371 (c)(1),
(2) Date: Jan. 19, 2021

(87) PCT Pub. No.: WO2020/087187
PCT Pub. Date: May 7, 2020

(65) Prior Publication Data
US 2021/0270766 A1 Sep. 2, 2021

Related U.S. Application Data

(60) Provisional application No. 62/755,148, filed on Nov. 2, 2018, provisional application No. 62/786,180, filed
(Continued)

(51) Int. Cl.
*G01N 33/487* (2006.01)
*G01N 27/327* (2006.01)
(Continued)

(52) U.S. Cl.
CPC ... *G01N 33/48785* (2013.01); *G01N 27/3278* (2013.01); *G16H 40/20* (2018.01);
(Continued)

(58) Field of Classification Search
None
See application file for complete search history.

(56) References Cited

U.S. PATENT DOCUMENTS 6,645,368 B1 * 11/2003 Beaty ................. G01N 27/3274
205/792
7,045,054 B1   5/2006 Buck et al.
(Continued)

FOREIGN PATENT DOCUMENTS

CA   3176542 A1 * 10/2021 ......... G01N 27/3273
EP   2967451 A1    1/2016
(Continued)

OTHER PUBLICATIONS

International Search Report and Written Opinion of the ISA/CA in PCT/CA2019/051567, dated Feb. 25, 2020; 17pgs.
(Continued)

*Primary Examiner* — J. Christopher Ball
(74) *Attorney, Agent, or Firm* — Haukaas Fortius PLLC; Michael Haukaas

(57) ABSTRACT

An electrochemical-sensor structure having a substrate and a nanostructured-sensing surface that receives a volume of a sample fluid. A sample region of the electrochemical-sensor structure for receiving the sample fluid volume is sized such that the volume of the fluid is sufficient to operatively cover a portion of the sample region of the electrochemical-sensor structure including the nanostructured-sensing surface. The electrochemical-sensor structure is connectable to a portable point-of-care (PoC) device. The PoC device may detect the energy properties of the sample fluid from the sample region
(Continued)

of the electrochemical-sensor structure, to produce a signal comprising a fluid reading wherein the fluid reading is related to the energy properties of a biomarker in the sample fluid thereby indicating the presence, the absence, or the quantity of the biomarker in the sample fluid.

22 Claims, 23 Drawing Sheets

Related U.S. Application Data on Dec. 28, 2018, provisional application No. 62/875,131, filed on Jul. 17, 2019.

(51) Int. Cl.
  *G06V 10/22* (2022.01)
  *G16H 40/20* (2018.01)
  *G16H 40/67* (2018.01)
  *G16H 50/20* (2018.01)
(52) U.S. Cl.
  CPC ............. *G16H 40/67* (2018.01); *G16H 50/20* (2018.01); *G06V 10/225* (2022.01)

(56) References Cited

U.S. PATENT DOCUMENTS

| | | | |
|---|---|---|---|
| 7,723,099 B2 | 5/2010 | Miller et al. | |
| 7,910,352 B2 | 3/2011 | Miller et al. | |
| 8,158,430 B1 | 4/2012 | Roy et al. | |
| 8,249,547 B1 | 8/2012 | Fellner | |
| 8,653,833 B2 | 2/2014 | Chodavarapu et al. | |
| 8,663,442 B2 | 3/2014 | Burke et al. | |
| 9,080,883 B2 | 7/2015 | Frey | |
| 9,869,669 B2 | 1/2018 | Han et al. | |
| 2007/0021805 A1* | 1/2007 | Kelety ................... C12Q 1/001 607/62 |
| 2011/0132778 A1* | 6/2011 | Austera .................... G06K 7/14 205/792 |
| 2013/0183243 A1 | 7/2013 | LaBelle et al. | |
| 2014/0374276 A1* | 12/2014 | Guthrie .................. G16H 10/60 204/403.14 |
| 2015/0083613 A1 | 3/2015 | Lee et al. | |
| 2015/0371350 A1 | 12/2015 | Zebarjadi et al. | |
| 2016/0057565 A1 | 2/2016 | Gold | |
| 2016/0202250 A1 | 7/2016 | Sharma et al. | |
| 2017/0024531 A1 | 1/2017 | Malaviya | |
| 2018/0067071 A1 | 3/2018 | Wu et al. | |
| 2019/0076068 A1 | 3/2019 | Yang et al. | |

FOREIGN PATENT DOCUMENTS

| | | |
|---|---|---|
| WO | 2007110779 A2 | 10/2007 |
| WO | 2016110804 A1 | 7/2016 |
| WO | 2017015172 A1 | 1/2017 |
| WO | 2017216339 A1 | 12/2017 |
| WO | 2018107143 A1 | 6/2018 |
| WO | 2018153919 A1 | 8/2018 |

OTHER PUBLICATIONS

Official Action in Canadian Patent Application No. 3060849, dated Aug. 28, 2020, 3pgs.
Official Action in Canadian Patent Application No. 3060849, dated Feb. 25, 2021, 4pgs.

* cited by examiner

PORTABLE ELECTROCHEMICAL-SENSOR SYSTEM FOR ANALYZING USER HEALTH CONDITIONS AND METHOD THEREOF

CROSS-REFERENCE TO RELATED APPLICATIONS

This application is a National Stage filing under 35 U.S.C. § 371 of International Application No. PCT/CA2019/051567, filed Nov. 4, 2019, which claims the benefit of U.S. Provisional Patent Application Ser. No. 62/755,148, filed Nov. 2, 2018, U.S. Provisional Patent Application Ser. No. 62/786,180, filed Dec. 28, 2018, and U.S. Provisional Patent Application Ser. No. 62/875,131, filed Jul. 17, 2019, the content of each of which is incorporated herein by reference in its entirety.

FIELD OF THE DISCLOSURE

The present disclosure relates generally to a portable electrochemical-sensor system and method for analyzing and monitoring a user's health conditions, and in particular, to a portable electrochemical-sensor system having a point-of-care (PoC) device and disposable electrochemical-sensor structures for analyzing and monitoring a user's health conditions by detecting one or more biomarkers and/or or disease-analytes in the patient's bodily fluid received onto the electrochemical-sensor structure. The PoC device also relates to providing geospatial health care to patients. In case of emergency, the PoC device may send geospatial information to the nearest emergency services, or shares information to the user's emergency contacts.

BACKGROUND

The focus of diagnostic medicine has shifted from hospital-based testing to simple home-based testing and has resulted in patient's increased awareness of their lifestyle. For example, portable health-monitoring devices such as blood-pressure monitors, blood-glucose meters, smart-watches with heart-rate monitors, and the like, have been widely used by patients to monitor their health conditions without going to clinics, medical labs, and/or hospitals for testing and diagnosis. Such portable health-monitoring devices enable home-based testing and significantly save patient's time for visiting doctors and medical labs, thereby improving their quality of life. Such portable health-monitoring devices also significantly save the resources of clinics, medical labs, and hospitals.

Portable health-monitoring devices may be hand-held devices allowing a convenient analysis of a user's health conditions. Examples of such portable health-monitoring devices include Ascensia™ BREEZE™ diabetes care system (Ascensia and BREEZE are trademarks of Ascensia Diabetes Care Holdings AG of Basel, Switzerland) and the GLUCOMETER ELITE® blood-glucose meter (GLUCOMETER ELITE is a trademark of Ascensia Diabetes Care Holdings AG of Basel, Switzerland).

Some types of portable health-monitoring devices such as blood-glucose meters, diagnose and monitor patients' health conditions by detecting and measuring the quantity of a biomarker (such as glucose) or disease-analyte (such as protein, nucleic acid molecules, ionic metabolites, and the like) in samples of a patient's bodily fluids. A biomarker is one or more specific compounds in a patient's bodily fluids that are indicative of certain health conditions.

There exist a plurality of biomarkers in human bodily fluids. However, in a home-based testing environment, there usually is a limited amount of bodily fluid sample available for a portable health-monitoring device to process. Furthermore, the quantity of a particular biomarker in a fluid sample may be very low. Therefore, it is always a challenge for a portable health-monitoring device and sampling structure to collect, detect, and measure biomarkers found in bodily fluids with sufficient accuracy for determining the patient's health condition.

Moreover, while existing portable health-monitoring devices such as a glucose-monitoring device can only detect a single biomarker from a bodily fluid sample, there exists a need for a portable health-monitoring device capable of detecting more than one biomarker for patients' convenience and for reducing the patients' healthcare costs.

There is also a need for diagnostic bio-sensing devices (also denoted as point-of-care (PoC) devices hereinafter) to reduce the burden on the existing healthcare system and to improve patient access to healthcare. Moreover, there is a demand for the development of PoC devices used by untrained consumers for home-based testing of physiological fluids for effectively diagnosing or predicting disease and for enhancing disease management. More particularly, there is a high demand for on-demand, portable, reliable, intuitive, and low-cost PoC devices for home-based testing for disease diagnosis and prognoses.

For example, the standard of care for heart failure in the art is retroactive rather than proactive in delivering healthcare services. After being diagnosed with heart failure, patients usually have to routinely visit their healthcare provide (HCP) for lab testing which is a time consuming burden on the patients and ineffective as the patients may be at risk between visits.

While sorely needed, a portable, at-home testing is only part of a complete solution. To have any meaningful impact on a patient's health, especially in times of emergency, the patient needs to have an option to access emergency health care services as, for example, emergent issues such as heart failure may lead to progressively debilitating conditions and sudden life-threatening events. Therefore, a solution is needed for improving emergency access involving patient's location, historical patient data, and communication when a patient is unresponsive. However, current diagnostic devices are limited in communicating with emergency services even in a situation that requires immediate medical attention, which may put patients in life-threatening risks in emergent situations.

U.S. Pat. No. 9,869,669 to Han, et al. teaches a sensor platform that includes a substrate, a plurality of nanochannels disposed on the substrate, and a plurality of electrodes, a waveguide disposed on the substrate and an analysis chamber and a reference chamber disposed on the substrate. Each electrode extends substantially across a width of the plurality of nanochannels. At least one analysis optical-resonator is disposed in the analysis chamber and is optically coupled to at least a portion of the waveguide. The at least one analysis optical-resonator is in fluid communication with at least one of the plurality of nanochannels. At least one reference optical-resonator is disposed in the reference chamber and is optically coupled to at least a portion of the waveguide. The at least one reference optical-resonator is in fluid communication with at least one other of the plurality of nanochannels.

US Patent Application Publication No. 2016/0202250 A1 to Sharma, et al. teaches a metal nanoparticles/single-walled carbon-nanotube (MNP/SWCNT) hybrid based chemiresistive biosensor for the quantitative detection of human cardiac biomarkers troponin I (cTnI) and myoglobin (Mb). The highly specific cardiac-antibody, anti-cTnI (Ab-cTnI) or anti-Mb (Ab-Mb), was covalently immobilized to site-specific carboxyl groups on MNP anchored over SWCNT device. The biosensor device was characterized by the source-drain current-voltage measurements. The device performance was investigated with a change in conductance in SWCNT channel upon exposure to cTnI in human serum. MNP provided large surface area for high protein loading and improved electrical signal by inducing charge density in SWCNT, resulting in low level detection of cTnI and Mb with high sensitivity.

US Patent Application Publication No. 2015/0083613 A1 to Lee, et al. teaches an electrochemical biosensor with improved hematocrit-measurement accuracy for measuring blood glucose. According to US 2015/0083613, an electrochemical biosensor including a first electrode part for correcting a measured hematocrit value and a second electrode part for measuring a glucose concentration is effective in improving accuracy of a measured hematocrit value and in more improving accuracy of a measured blood-glucose concentration using the measured hematocrit values for correction, because an insulation cover is made thinner than a working electrode and an auxiliary electrode, so that areas of a first working electrode and a first auxiliary electrode of the first electrode part exposed to a blood sample become equal, a distance between the first working electrode and the second working electrode becomes constant, and electrode areas are maintained constantly by the insulation cover even when a positioning error occurs during printing.

U.S. Pat. No. 7,045,054 B1 to Buck, et al. teaches sensors and a method for detecting an analyte. The sensors each have a volume of a hydrophilic medium that retains an amount of analyte proportionate to the concentration of analyte in a biological fluid, electrodes and a redox enzyme in contact with medium, and an electron transfer mediator. The fluid contacts sensors and at initially predetermined intervals intermittently applies a potential to electrode sufficient to oxidize the mediator and sensing current through electrode as a function of the duration of the applied potential. The applied mediator oxidizing applied potential is maintained for a period of time sufficient to determine the rate of change of current with time through electrode. The current flow is correlated with the current flow for known concentrations of the analyte in medium.

US Patent Application Publication No. 2018/0067071 A1 to Wu, et al. teaches biosensor systems including a measurement device and test sensors including at least three independently addressable electrodes, with at least two of the electrodes being substantially chemically isolated. One or more working electrodes may be combined with two or more counter electrodes. The two or more counter electrodes may operate at different potentials to provide for multi-analyte electrochemical analysis. Analysis methods are provided to perform multi-analyte electrochemical analysis and test sensors are provided having resistance to chemical mixing between secondary analysis regions.

U.S. Pat. No. 7,723,099 B2 to Miller, et al. teaches an electrochemical immunosensor system with reduced interference which comprises: a first immunosensor that generates an electrochemical signal based on the formation of a sandwich between an immobilized antibody, a target analyte and a labeled antibody, wherein a portion of the signal arises from non-specific binding of the labeled antibody in the region of the first immunosensor, and a second immunosensor that acts as an immuno-reference sensor and generates a signal that is the same as or predictably related to the degree of non-specific binding which occurs in the region of the first immunosensor, and has an immunocomplex between an immobilized antibody and an endogenous or exogenous protein that is in the sample and that is not the target analyte.

US Patent Application Publication No. 2013/0183243 to Labelle, et al. teaches a diagnostic device and methods of using the same for diagnostic assays for monitoring the presence of biological samples wherein the device allows for the determination of at least two assay components on one sensor. More specifically, US 2013/0183243 relates to a multi-marker electrochemical impedance spectroscopy sensor comprising a plurality of molecular recognition elements wherein the sensor comprises multiple different molecular recognition element types that are tuned in a manner that alters the frequency of the molecular recognition element type such that it is at a detectably different frequency to the frequency of other molecular recognition element types on the same sensor.

U.S. Pat. No. 7,910,352 B2 to Miller, et al. teaches an electrochemical immunosensor system with reduced interference. The system comprises a first immunosensor that generates an electrochemical signal based on the formation of a sandwich between an immobilized antibody, a target analyte and a labeled antibody, wherein a portion of the signal arises from non-specific binding of the labeled antibody in the region of the first immunosensor, and a second immunosensor that acts as an immuno-reference sensor and generates a signal that is the same as or predictably related to the degree of non-specific binding which occurs in the region of the first immunosensor, and has an immunocomplex between an immobilized antibody and an endogenous or exogenous protein that is in the sample and that is not the target analyte.

US Patent Application Publication No. 2019/0076068 A1 to Yang, et al. teaches a diagnostic Electrochemical Impedance Spectroscopy (EIS) procedure applied to measure values of impedance-related parameters for one or more sensing electrodes. The parameters may include real impedance, imaginary impedance, impedance magnitude, and/or phase angle. The measured values of the impedance-related parameters are then used in performing sensor diagnostics, calculating a highly-reliable fused sensor glucose value based on signals from a plurality of redundant sensing electrodes, calibrating sensors, detecting interferents within close proximity of one or more sensing electrodes, and testing surface area characteristics of electroplated electrodes. Impedance-related parameters can be defined that are substantially glucose-independent over specific ranges of frequencies. An Application Specific Integrated Circuit (ASIC) enables implementation of the EIS-based diagnostics, fusion algorithms, and other processes based on measurement of EIS-based parameters.

U.S. Pat. No. 8,653,833 B2 to Chodavarapu, et al. teaches a system comprising: (a) a signal generator, the signal generator for generating a probe signal having at least one predetermined characteristic and comprising at least a digital to analog converter; (b) a signal converter, the signal converter for generating a digital representation of at least one analog input signal of a plurality of analog input signals and comprising at least one of an analog to digital converter and a multiplexer; (c) a sensor, the sensor comprising at least a first electrical contact and a second electrical contact; (d) a reference impedance; (e) a switch, the switch for receiving the probe signal from the signal generator and applying the probe signal at least one of continuously and selectively to at least one of the first electrical contact of the sensor and the reference impedance; (f) an impedance connect circuit, the impedance connect circuit comprising at least a switch for selectively connecting at least one of the second electrical contact of the sensor and the reference impedance to the signal converter; (g) an analysis circuit, the analysis circuit for receiving at least a digital representation of the generated probe signal and a digital representation of the at least one analog input signal, performing a first process upon the digital representation of the generated probe signal to determine at least a characteristic of the probe signal, performing a second process upon the digital representation of the at least one analog input signal in dependence upon at least the determined characteristic of the probe signal to generate at least one of a real component and an imaginary component of the digital representation of the at least one analog input signal, applying a correction to at least the imaginary component, and determining an impedance of the sensor in dependence upon at least the reference impedance and the at least one of the real component and the imaginary component of the digital representation of the at least one analog input signal; and (h) a first memory, the first memory for storing the determined impedance for subsequent retrieval.

U.S. Pat. No. 8,663,442 B2 to Burke, et al. teaches a method of measuring an analyte in a biological fluid comprises applying an excitation signal having a DC component and an AC component. The AC and DC responses are measured; a corrected DC response is determined using the AC response; and a concentration of the analyte is determined based upon the corrected DC response.

U.S. Pat. No. 8,158,430 B1 to Roy, et al. teaches fluidic devices and systems that allow detection of analytes from a biological fluid for providing point-of-care testing for a variety of medical applications.

EP 2,967,451 B1 to Johnson, et al. teaches 2014/144660 point of care sensor systems that include portable readers and disposable cartridges for receiving and analyzing samples. A cartridge may be equipped with one or more sensor channels, each containing one or more sensors. After providing a sample to a cartridge, the cartridge can be inserted into a reader, which can interact with the cartridge to perform on-cartridge sensing and receive signals indicating the presence and/or quantity of one or more targets in the sample. Examples of cartridges can include cardiac panels, sepsis panels and the like. In some embodiments, the same sensor hardware may be configured for multiple measurements of different targets conducted at different time frames. On-cartridge solid and liquid reagent storage and delivery mechanisms are also disclosed therein.

US Patent Application Publication No. 2016/0057565 A1 to Gold teaches systems and methods that sense, communicate and process one or more of a user's physiologic parameters, such as during a time when the user is in proximity with an object of interest. Objects may be products, locations and other people. One embodiment thereof enables users, designers, manufacturers, marketers and sellers to secure valuable information about how an object is (or many object are) perceived and used by a user (or many users). Various embodiments thereof may be used in conjunction with smart objects (e.g., Internet-connected objects) and dumb objects (e.g., objects having no Internet or other network connection).

US Patent Application Publication No. 2015/0371350 A1 to Zebarjadi, et al. teaches a system in which a patient may request medical services from a patient computing device. Doctors may be matched with patients desiring or needing medical care. A patient may enroll or subscribe with a system using a computing device. Using the same or a different computing device, a patient may request medical care at a particular location. A doctor may be matched to a patent request for medical services. Doctor/patient matches may be made based upon location information, the medical needs of the patient, the medical practice of the doctor, gender, language skills, or any other criteria. A doctor may accept or decline a request for medical services from a patient. A bi-directional and at least partially anonymized communication may be initiated to permit a doctor to evaluate the medical needs of a patient. Computing devices associated with a patient and/or doctor may be used in conjunction with a coordination component to collect relevant information, record medical records, manage communications, process billing, navigating to a patient's location, and/or other purposes.

U.S. Pat. No. 9,080,883 B2 to Frey teaches a method of dynamic output of information for the evacuation of persons, in particular from buildings, to a portable device based on current position data of the device as determined by a position determination system. The current usability of escape routes located in the building is determined by a sensor system. Evacuation information is determined by a control unit, based on the current usability of the escape routes and the current position of the device and output on the portable device. In emergency situations, dedicated evacuation information can thus be determined for a person as a function of the whereabouts of the person and the respective hazardous situation and output on the mobile device (e.g. smartphone, PDA) of the person, which enables, inter alia, a rapid and efficient evacuation of the building or a site.

US Patent Application Publication No. 2017/0024531 A1 to Malaviya teaches a healthcare information system for providing near-real or real-time contact tracing. The system comprises: a position data receiver unit configured to receive position data related to one or more entities associated with a healthcare facility; a contextual profile management unit configured to utilize received position data to generate, maintain or update one or more contextual profiles, each of the one or more contextual profiles corresponding to each of the one or more entities. Devices, systems and methods are provided related to the use of near-real or real-time contact tracing in applications including infection control, developing infection pathways, among others.

U.S. Pat. No. 8,249,547 B1 to Fellner teaches a wearable emergency alert device including a wearable member and a separately encased mobile phone member that is selectively attachable to the wearable member. The wearable member includes an attachment member for attaching the wearable member to a body part of the user, a first transmitter for sending a first signal to the mobile phone member, a power source for the first transmitter and a first actuator operable by a user for actuating the first transmitter to send a signal to the mobile phone member. The mobile phone member includes a mobile phone transceiver for establishing a first communication link between the mobile phone transceiver and the first transmitter; and the second communication link between the mobile phone transceiver and a remote receiver for transmitting and receiving at least one of data, voice and messages between the mobile phone transceiver and a remote receiver. A mounting member is provided for selectively removably mounting the mobile phone member to the wearable member, and permitting the mobile phone member to engage the first actuator to actuate an emergency signal.

SUMMARY

Embodiments disclosed herein relate to a portable electrochemical-sensor system and method for analyzing and monitoring a user's health conditions. In some embodiments, the portable electrochemical-sensor system uses biosensors for detecting the presence of one or more analytes or biomarkers from body fluids.

As those skilled in the art will understand, an analyte is a chemical component, constituent, or species that is of interest in an analytical procedure being conducted on a sample. The term "analyte" often refers to relatively simple elements or molecules such as serum chloride or liver enzymes that are detectable in an analytic process.

Those skilled in the art will also understand that a biomarker is biological molecule typically found in blood, other body fluids, or tissues that may be used as a sign of a normal or abnormal process, or of a condition or disease. A biomarker has a detectable characteristic that may be objectively measured and evaluated as an indicator of normal biologic processes, pathogenic processes, or pharmacologic response to a therapeutic intervention. The term "biomarker" often refers to markers for detecting or diagnosing specific diseases or groups of diseases which may be malignant lesions or non-malignant diseases such as cardiovascular disease.

Notwithstanding the above differences, those skilled in the art will appreciate that the electrochemical-sensor system and method described herein may be adapted to detect suitable analytes and/or biomarkers in various embodiments. Therefore, in the description hereinafter, the terms "analyte" and "biomarker" may be used interchangeably.

According to one aspect of this disclosure, a portable electrochemical-sensor system comprises a point-of-care (PoC) device and disposable electrochemical-sensor structures for analyzing and monitoring the health conditions of a user or patient.

In some embodiments, the PoC device collaborates with the disposable electrochemical-sensor structure for detecting and collecting information from biomarkers found in mammalian body fluid samples.

In some embodiments, the electrochemical-sensor structure comprises a sample region for receiving a patient's bodily fluid samples. The electrochemical-sensor structure may be inserted into otherwise coupled to the PoC device. The PoC device then detects and measure the quantity of one or more biomarkers and/or or disease-analytes indicative of health conditions in the received bodily fluid samples by measuring the energy property of the sample fluid. In some embodiments, analyte concentrations are quantified electrochemically and noise from undesirable proteins is reduced by the introduction of a filtration unit.

With the portable electrochemical-sensor system disclosed herein, it may be possible to diagnose certain illnesses without an in-person meeting with a physician, and the user may avoid making a visit to the clinic or hospital for simple diagnostic tests such as finger-prick blood tests, thereby reducing the user's wait time at clinics and the time spent by healthcare professionals for performing such simple diagnostic tests.

The portable electrochemical-sensor system disclosed herein is suitable for use by untrained users for home-based testing of physiological fluids for effectively diagnosing or predicting diseases and for enhancing disease management.

The portable electrochemical-sensor system disclosed herein is efficient in monitoring patient's health conditions by detecting one or more analytes in the bodily fluid received onto the electrochemical-sensor structure. Related methods and components of the portable electrochemical-sensor system for precisely detecting the analytes are also disclosed.

According to one aspect of this disclosure, the portable electrochemical-sensor system comprises a PoC device acting as a reader and a sensor strip.

In various embodiments, the sensing strip may comprise single or multiple working electrodes (WE) along with corresponding counter and reference electrodes (CE and RE respectively). Separation unit HF-PSC is also disclosed here which is proficient in trapping cellular components from the body fluids. The electrochemical sensor is connected to a portable PoC device. The PoC device may detect the energy properties of the sample fluid from the sample region of the electrochemical-sensor structure, to produce a signal comprising a fluid reading wherein the fluid reading is related to the energy properties of an analyte in the sample fluid thereby indicating the presence, absence, or the quantity of analyte in the sample fluid.

The PoC devices disclosed herein measure the quantity of specific biomarkers in bodily fluids that are indicative of health conditions. By using the PoC device, a user may diagnose certain illnesses without an in-person meeting with a physician.

In some embodiments, the electrochemical-sensor structure or strip comprises one or more electrodes, a flexible substrate, a top cover layer, and a hydrophobic isolating layer. A sample fluid may be placed onto a sample region of the strip, and the strip is then inserted into the PoC device. The PoC device determines the presence and/or quantity of a particular analyte in the sample fluid by measuring the energy property of the sample fluid.

According to one aspect of this disclosure, there is disclosed an apparatus for analyzing a bodily fluid sample of a user. The apparatus comprises: a housing comprising at least one first port for receiving an electrochemical-sensor structure, the electrochemical-sensor structure comprising a first circuitry having a first set of electrodes for contacting the bodily fluid sample; an identification circuitry for identifying one or more biomarkers analyzable using the electrochemical-sensor structure; an analysis circuitry comprising a set of coupling electrodes for electrically coupling to the first set of electrodes of the electrochemical-sensor structure for analyzing the identified one or more biomarkers in the bodily fluid sample; a control circuitry coupled to the identification and analysis circuitries for determining a set of bio-sensing parameters based on the identified one or more biomarkers and for controlling the analysis circuitry to analyze the identified one or more biomarkers in the bodily fluid sample based on the set of bio-sensing parameters; and an output for outputting an analytical result of said analysis of the identified one or more biomarkers in the bodily fluid sample.

In some embodiments, the identification circuitry is for identifying the one or more biomarkers by measuring an impedance of a second circuitry of the electrochemical-sensor structure, the resistance of the second circuitry encoding identities of the one or more biomarkers.

In some embodiments, the second circuitry comprises a second set of electrodes.

In some embodiments, the identification circuitry is for identifying the one or more biomarkers by reading a radio frequency identification (RFID) tag encoding identities of the one or more biomarkers of the electrochemical-sensor structure.

In some embodiments, the RFID tag is on the electrochemical-sensor structure or on a carrying vial accommodating the electrochemical-sensor structure.

In some embodiments, the apparatus further comprises an imaging component; and the identification circuitry is for identifying the one or more biomarkers by using the imaging component to scan an image encoding identities of the one or more biomarkers.

In some embodiments, the identification circuitry is for commanding a device having an imaging component and functionally coupled to the apparatus to use the imaging component to scan an image encoding identities of the one or more biomarkers for identifying the one or more biomarkers.

In some embodiments, the image is a one-dimensional barcode or a two-dimensional barcode.

In some embodiments, the image is on the electrochemical-sensor structure or on a carrying vial accommodating the electrochemical-sensor structure.

In some embodiments, the analysis circuitry is configured for measuring one or more impedances, one or more currents, and/or one or more voltages of the first circuitry for analyzing the identified one or more biomarkers in the bodily fluid sample.

In some embodiments, the analysis circuitry comprises at least one potentiostat circuitry for electrically coupling to the first circuitry for analyzing the identified one or more biomarkers in the bodily fluid sample.

In some embodiments, the at least one potentiostat circuitry comprises a Direct-Current (DC) potentiostat circuitry, an Alternate-Current (AC) potentiostat circuitry, or a combination thereof.

In some embodiments, the set of coupling electrodes comprise at least a coupling reference-electrode (RE), a coupling control-electrode (CE), and a coupling working-electrode (WE) for electrically coupling to a RE, a CE, and a WE of the electrochemical-sensor structure.

In some embodiments, the set of coupling electrodes comprise at least a coupling RE, a coupling CE, and a plurality of coupling WEs for electrically coupling to a RE, a CE, and a plurality of WEs of the electrochemical-sensor structure.

In some embodiments, the set of coupling electrodes comprise at least a coupling RE, a coupling CE, and more than two coupling WEs for electrically coupling to a RE, a CE, and more than two WEs of the electrochemical-sensor structure.

In some embodiments, a first set of at least one of the coupling WEs are for electrically coupling to a first set of WEs of the electrochemical-sensor structure oversaturated with a first set of one or more capture ligands; a second set of at least one of the coupling WEs are for electrically coupling to a second set of WEs of the electrochemical-sensor structure cross-linked with predefined concentration of a second set of one or more capture ligands; and the analysis circuitry is for analyzing the identified one or more biomarkers in the bodily fluid sample by calculating analyte concentration based on the difference of the charge transfer resistances (RCTs) between the first and second sets of WEs of the electrochemical-sensor structure.

In some embodiments, the analysis circuitry is for analyzing the identified one or more biomarkers in the bodily fluid sample by calculating analyte concentration based on the difference of the charge transfer resistances (RCTs) between the first and second sets of WEs of the electrochemical-sensor structure and using a statistical method.

In some embodiments, the output comprises a screen for displaying the analytical result.

In some embodiments, the screen is a touchscreen for displaying the analytical result and for receiving input from the user.

In some embodiments, the output comprises a speaker for outputting the analytical result.

In some embodiments, the apparatus further comprises a networking module for communication with one or more remote devices.

In some embodiments, the networking module is a BLUETOOTH module.

In some embodiments, the output comprises the networking module is for outputting the analytical result to the one or more remote devices.

In some embodiments, the one or more remote devices comprise an artificial intelligence (AI) system for determining the user's health condition based on the analytical result.

In some embodiments, the apparatus further comprises one or more buttons for receiving input from the user.

In some embodiments, the one or more buttons comprises a SOS button for initiating an emergent communication with one or more emergency services.

In some embodiments, the housing comprises a front wall, a rear wall, a top wall, a bottom wall, and two opposite sidewalls; and the one or more buttons are distributed on at least one of the sidewalls.

In some embodiments, the at least one first port is located on the top wall or the bottom wall.

In some embodiments, the apparatus further comprises an adaptor for electrically removably coupling to the apparatus, said adaptor comprising a plurality of second ports for receiving a plurality of additional electrochemical-sensor structures.

In some embodiments, the plurality of additional electrochemical-sensor structures have a same mechanical specification and/or a same electrical specification.

In some embodiments, the plurality of additional electrochemical-sensor structures have different mechanical specifications and/or different electrical specifications.

In some embodiments, the apparatus comprises a plurality of first ports.

In some embodiments, the plurality of first ports have a same mechanical specification and/or a same electrical specification.

In some embodiments, the plurality of first ports have different mechanical specifications and/or different electrical specifications.

In some embodiments, the apparatus further comprises: a battery for powering at least the identification circuitry, the analysis circuitry, and the control circuitry; and a second port for electrically coupling to a power source for charging the battery.

In some embodiments, the second port is a Universal Serial Bus (USB) port.

In some embodiments, the apparatus further comprises a third port for physically and electrically coupling to a smartphone.

In some embodiments, the analysis circuitry and/or the control circuitry comprise an electrochemical module for detecting and analyzing N-terminal Pro B-type natriuretic peptide (NT-pro-BNP), a fluorescence module and a polymerase chain reaction (PCR) module for detecting and analyzing aptamer-based ligand, and an absorbance module for metabolite analysis.

In some embodiments, the analysis circuitry and/or the control circuitry further comprise a memory storing therein a calibration curve for determining concentration of the identified one or more biomarkers.

In some embodiments, the apparatus further comprises one or more global navigation satellite system (GNSS) components for obtaining geospatial information of the apparatus; and the output is for outputting the analytical result and the geospatial information.

In some embodiments, the one or more remote devices are for: assessing the analytical result to obtain an assessment of the user's health condition; storing the analytical result, the geospatial information, and the assessment of the user's health condition; notifying the user for further action if the assessment of the user's health condition is above a first threshold but below a second threshold; and initiating an emergency protocol if the assessment of the user's health condition is above the second threshold.

According to one aspect of this disclosure, there is disclosed an apparatus for analyzing a bodily fluid sample of a user. The apparatus comprises: a housing comprising at least one first port for receiving an electrochemical-sensor structure, the electrochemical-sensor structure comprising a first circuitry having a first set of electrodes for contacting the bodily fluid sample; an analysis circuitry comprising a set of coupling electrodes for electrically coupling to the first set of electrodes of the electrochemical-sensor structure for analyzing one or more biomarkers in the bodily fluid sample; and an output for outputting an analytical result of said analysis of the identified one or more biomarkers in the bodily fluid sample. The set of coupling electrodes comprise at least a coupling reference-electrode (RE), a coupling control-electrode (CE), and a plurality of coupling working-electrodes (WEs) for electrically coupling to a RE, a CE, and a plurality of WEs of the electrochemical-sensor structure.

In some embodiments, the set of coupling electrodes comprise at least a coupling RE, a coupling CE, and more than two coupling WEs for electrically coupling to a RE, a CE, and more than two WEs of the electrochemical-sensor structure.

In some embodiments, a first set of at least one of the coupling WEs are for electrically coupling to a first set of WEs of the electrochemical-sensor structure oversaturated with a first set of one or more capture ligands; a second set of at least one of the coupling WEs are for electrically coupling to a second set of WEs of the electrochemical-sensor structure cross-linked with predefined concentration of a second set of one or more capture ligands; and the analysis circuitry is for analyzing the identified one or more biomarkers in the bodily fluid sample by calculating analyte concentration based on the difference of the charge transfer resistances (RCTs) between the first and second sets of WEs of the electrochemical-sensor structure.

In some embodiments, the analysis circuitry is for analyzing the identified one or more biomarkers in the bodily fluid sample by calculating analyte concentration based on the difference of the charge transfer resistances (RCTs) between the first and second sets of WEs of the electrochemical-sensor structure and using a statistical method.

According to one aspect of this disclosure, there is disclosed an electrochemical-sensor structure comprising: a substrate; a first circuitry comprising a first set of electrodes distributed on the substrate and extending into a sampling region of the substrate for contacting a bodily fluid sample; and an identification structure for identifying one or more biomarkers of the bodily fluid sample analyzable using the electrochemical-sensor structure.

In some embodiments, the substrate comprises a polymer.

In some embodiments, the polymer comprises a polystyrene, a polyester, a polycarbonate, or a polyamide.

In some embodiments, the substrate is a porous substrate.

In some embodiments, the substrate is a track-etched membrane having a porosity equal to or greater than 30%.

In some embodiments, the substrate comprises a Poly (methyl methacrylate) (PMMA) membrane.

In some embodiments, the identification structure comprises a second circuitry having a predefined impedance encoding identities of the one or more biomarkers of the electrochemical-sensor structure.

In some embodiments, the identification structure comprises a radio frequency identification (RFID) tag encoding identities of the one or more biomarkers of the electrochemical-sensor structure.

In some embodiments, the identification structure comprises an image encoding identities of the one or more biomarkers of the electrochemical-sensor structure.

In some embodiments, the image comprises a one-dimensional barcode or a two-dimensional barcode encoding identities of the one or more biomarkers of the electrochemical-sensor structure.

In some embodiments, the first set of electrodes comprise at least a reference electrode (RE), a control electrode (CE), and a working electrode (WE).

In some embodiments, the first set of electrodes comprise at least a RE, a CE, and a plurality of WEs.

In some embodiments, the first set of electrodes comprise at least a RE, a CE, and more than two WEs.

In some embodiments, a first set of at least one of the WEs are oversaturated with a first set of one or more capture ligands and a second set of at least one of the WEs are cross-linked with predefined concentration of a second set of one or more capture ligands.

In some embodiments, the first set of one or more capture ligands comprise a same capture ligand.

In some embodiments, the first set of one or more capture ligands comprise different capture ligands.

In some embodiments, the second set of one or more capture ligands comprise a same capture ligand.

In some embodiments, the second set of one or more capture ligands comprise different capture ligands.

In some embodiments, the first set of one or more capture ligands are the same as the second set of one or more capture ligands.

In some embodiments, the first set of one or more capture ligands are different to the second set of one or more capture ligands.

In some embodiments, each of the first set of electrodes comprises a layer of chromium (Cr) and a layer of gold (Au) on top of the Cr layer.

In some embodiments, at least one WE further comprises a layer of conductive nano-material on top of the Au layer.

In some embodiments, the at least one WE further comprises a layer of detection element on top of the layer of conductive nano-material.

In some embodiments, the CE extends along at least two edges of the sampling region thereby encircling the rest of the first set of electrodes.

In some embodiments, the electrochemical-sensor structure further comprises: a hydrophobic middle layer having a distal-end opening forming a sampling port for receiving the bodily fluid sample into the sampling region; and a protection layer on top of the hydrophobic middle layer and covering the sampling region.

In some embodiments, the sampling region of the substrate comprises: one or more introductory channels about an edge thereof for introducing the bodily fluid sample using the capillary effects; a heterophile plasma separating component (HF-PSC) unit adjacent the one or more introductory channels for receiving the bodily fluid sample therefrom and filtering out interfering components of the bodily fluid sample; and an analyte-drop chamber intermediate the HF-PSC and the first set of electrodes, the analyte-drop chamber receiving the filtered bodily fluid sample from the HF-PSC for allowing the filtered bodily fluid sample to contact the first set of electrodes.

In some embodiments, at least one of the one or more introductory channels is of a funnel shape and comprises an opening adjacent the edge of the sampling region and tapering towards the HF-PSC unit.

In some embodiments, at least one of the one or more introductory channels is engraved on the substrate.

In some embodiments, at least one of the one or more introductory channels is formed by a gap in a coating on the substrate.

In some embodiments, the HF-PSC unit comprises symmetrical and/or asymmetrical pores with varied pore sizes.

In some embodiments, the electrochemical-sensor structure further comprises: one or more capillary channels each comprising an entrance in or about the analyte-drop chamber and extending from the analyte-drop chamber to the first set of electrodes; wherein at least one of the one or more capillary channels is hydrophilic to the bodily fluid sample and comprises an abrupt expansion at a distance to the entrance, for controlling a volume of the bodily fluid sample therein; and wherein at least one WE extends to the at least one of the one or more capillary channels at a location intermediate the entrance and the expansion thereof for interacting with the bodily fluid sample therein.

In some embodiments, the electrochemical-sensor structure further comprises one or more capillary channels each comprising an entrance in or about the analyte-drop chamber and extending from the analyte-drop chamber to the first set of electrodes; at least one of the one or more capillary channels is hydrophobic to the bodily fluid sample and comprises an abrupt tapering portion at a distance to the entrance, for controlling a volume of the bodily fluid therein; and at least one WE extends to the at least one of the one or more capillary channels at a location intermediate the entrance and the tapering portion thereof for interacting with the bodily fluid sample therein.

According to one aspect of this disclosure, there is disclosed an electrochemical-sensor structure comprising: a substrate; and a first circuitry comprising a first set of electrodes distributed on the substrate and extending into a sampling region of the substrate for contacting a bodily fluid sample. The first set of electrodes comprise at least a reference electrode (RE), a control electrode (CE), and a plurality of working electrodes (WEs).

In some embodiments, said plurality of WEs comprise more than two WEs.

In some embodiments, a first set of at least one of the WEs are oversaturated with a first set of one or more capture ligands and a second set of at least one of the WEs are cross-linked with predefined concentration of a second set of one or more capture ligands.

According to one aspect of this disclosure, there is disclosed an electrochemical-sensor structure comprising: a substrate; and a first circuitry comprising a first set of electrodes distributed on the substrate and extending into a sampling region of the substrate for contacting a bodily fluid sample. The sampling region of the substrate comprises: one or more introductory channels about an edge thereof for introducing the bodily fluid sample using the capillary effects; a heterophile plasma separating component (HF-PSC) unit adjacent the one or more introductory channels for receiving the bodily fluid sample therefrom and filtering out interfering components of the bodily fluid sample; and an analyte-drop chamber intermediate the HF-PSC and the first set of electrodes, the analyte-drop chamber receiving the filtered bodily fluid sample from the HF-PSC for allowing the filtered bodily fluid sample to contact the first set of electrodes.

In some embodiments, at least one of the one or more introductory channels is of a funnel shape and comprises an opening adjacent the edge of the sampling region and tapering towards the HF-PSC unit.

According to one aspect of this disclosure, there is disclosed an electrochemical-sensor structure comprising: a substrate; and a first circuitry comprising a first set of electrodes distributed on the substrate and extending into a sampling region of the substrate for contacting a bodily fluid sample; and one or more capillary channels each comprising extending from an entrance in the sampling region to the first set of electrodes. At least one of the one or more capillary channels comprises an area-changing portion at a distance to the entrance and having a changed cross-sectional area, for controlling a volume of the bodily fluid sample therein; and at least one WE extends to the at least one of the one or more capillary channels at a location intermediate the entrance and the area-changing portion thereof for interacting with the bodily fluid sample therein.

In some embodiments, the at least one of the one or more capillary channels is hydrophilic to the bodily fluid sample; and the area-changing portion of the at least one of the one or more capillary channels is a portion downstream of the at least one WE with an increased cross-sectional area.

In some embodiments, the at least one of the one or more capillary channels is hydrophobic to the bodily fluid sample; and the area-changing portion of the at least one of the one or more capillary channels is a portion downstream of the at least one WE with a decreased cross-sectional area.

According to one aspect of this disclosure, there is disclosed a system for analyzing a bodily fluid sample of a user. The system comprises: an electrochemical-sensor structure for receiving thereon the bodily fluid sample; and a testing apparatus collaborating with the electrochemical-sensor structure for analyzing the bodily fluid sample. The electrochemical-sensor structure comprises: a substrate, a first circuitry comprising a first set of electrodes distributed on the substrate and extending into a sampling region of the substrate for contacting a bodily fluid sample, and an identification structure for identifying one or more biomarkers of the bodily fluid sample analyzable using the electrochemical-sensor structure. The testing apparatus comprises: a housing comprising at least one first port for receiving the electrochemical-sensor structure, the electrochemical-sensor structure comprising a first circuitry having a first set of electrodes for contacting the bodily fluid sample, an identification circuitry for identifying one or more biomarkers analyzable using the electrochemical-sensor structure, an analysis circuitry comprising a set of coupling electrodes for electrically coupling to the first set of electrodes of the electrochemical-sensor structure for analyzing the identified one or more biomarkers in the bodily fluid sample, a control circuitry coupled to the identification and analysis circuitries for determining a set of bio-sensing parameters based on the identified one or more biomarkers and for controlling the analysis circuitry to analyze the identified one or more biomarkers in the bodily fluid sample based on the set of bio-sensing parameters; and an output for outputting an analytical result of said analysis of the identified one or more biomarkers in the bodily fluid sample.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced designate corresponding parts throughout the different views.

DETAILED DESCRIPTION

Overview

Figure 1A:
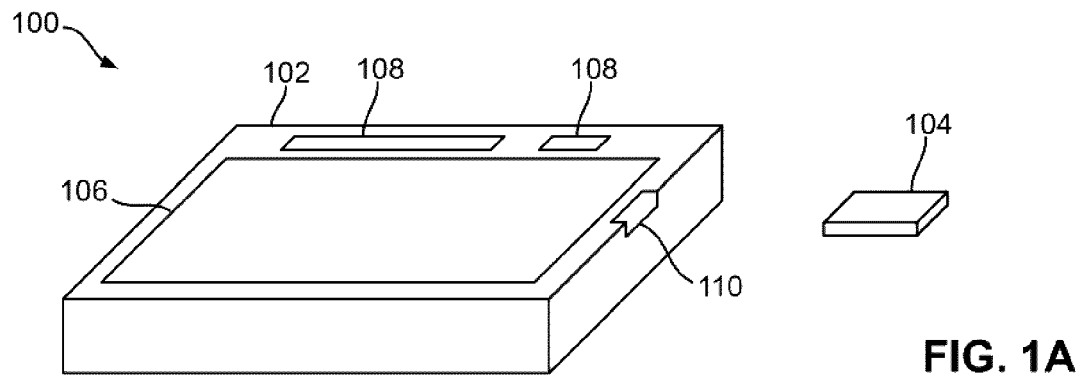
FIGS. 1A and 1B are schematic perspective and plan views, respectively, of a health monitoring system according to some embodiments of this disclosure, the portable health monitoring system comprising a portable point-of-care (PoC) device and an electrochemical-sensor structure.

Embodiments disclosed herein generally relate to a portable electrochemical-sensor system for monitoring a user's health conditions. More particularly, some embodiments disclosed herein relate to an on-demand, portable, reliable, intuitive, and low-cost bio-sensing device such as a point-of-care (PoC) device for home-based testing for disease diagnosis and prognosis. In some embodiments, the portable electrochemical-sensor system comprises diagnostic bio-sensing device and a sampling structure such as a disposable electrochemical-sensor structure, for monitoring a patient's health conditions by detecting various analyte such as proteins and other molecules in a sample of the patient's bodily fluid received onto the electrochemical-sensor structure. The presence, absence, or variation in the quantities of certain analyte in bodily fluids may be used as an indicator or predictor of disease.

In some embodiments, the electrochemical-sensor structure comprises a sample-receiving region for receiving a sample of the patient's bodily fluid. The sample-receiving region of the electrochemical-sensor structure may comprise a substrate with a plurality of electrodes and having one or more detection elements thereon suitable for detecting one or more analyte.

In some embodiments, the substrate may be made of a flexible polymeric material such as a flexible modified/unmodified (treated or untreated) acrylic or polymer membrane strip with one or more detection elements thereon for detecting one or more analyte.

In some embodiments, the PoC device may comprise one or more potentiostat circuitries for monitoring the electrochemical reaction between the analyte in the bodily fluid sample and the detection elements.

The potentiostat circuitries may comprise a DC potentiostat circuitry whose application can be confined to chronoamperometry and voltammetry, when used in combination with a frequency response analyzer, may be used as an impedance-analysis system.

In particular, the components of the system disclosed herein may be used to stimulate the sample with an AC, DC, or a combination of thereof. In some embodiments, the signal may constitute an AC amplitude with a specific frequency offset with a DC signal. The inspecting signal may also be generated in different combinations. For instance, an embodiment may simply use a DC signal for sample inspection resulting in a flow of current in either direction, thereby allowing for characterization, recognition, or analysis of the substrate. More specifically, the system uses a range of frequencies to gauge criteria related to, but not limited to, quality of substrate, conductance of the electrode, quality of the biosensor immobilized on the electrode, and binding efficiency of the analyte to the biosensor.

In some embodiments, the diagnosis of the system through electrochemical impedance spectroscopy (EIS) may be done through domain recognition aided by the resultant Nyquist-plot analysis. For instance, by relying on Nyquist-plot pre-characterization of the capture ligand on strips, newly scanned data may be used in comparison to gauge the quality of the immobilized layers after a certain duration in storage, or prior to use.

In these embodiments, the PoC device may comprise three electrodes used by a DC potentiostat circuitry coupled to a frequency-response analyzer. For example, the system may contain four stages: current-to-voltage conversion with a multiplexer, an amplifier to accommodate extra electrodes within the system, a gain stage, and an eventual frequency response analyzer integrated circuit (IC). In variations to the design, the multiplexer may be used to switch the system between a calibration mode and one or more multiple-electrode modes (e.g., a three-electrode mode, a four-electrode mode, . . . , and an eight-electrode mode).

When a bodily fluid sample is placed on the sample region of the electrochemical-sensor structure, electrochemical interaction between the analyte in the bodily fluid sample and the detection elements occur and cause the energy changes. The electrochemical-sensor structure is engaged with an ex vivo PoC device which imparts energy to the sample fluid and measures the energy properties of the sample for generating a sample-fluid reading indicative of the concentration of a specific compound in the sample fluid. The volume of the sample may be as small as about 10 microliters ($\mu$L) to about 20 $\mu$L. The imparted energy may be electrical energy and the measured energy property may be the potential difference, current, or impedance.

As an analyte often possesses an affinity and specificity to a particular detection element, an electrochemical-sensor structure generally needs to be specifically manufactured for detection of a particular type of analyte.

Antibodies, nucleic acid aptamers and enzymes are often used as detection elements of bio-sensing devices because of their high specificity and affinity for respective biomarkers. Given the high specificity of a detection element to a particular analyte, the sampling region of a device may only contain one type of detection element and may be used to detect a single analyte. Moreover, different analytes possess different energy properties. Accordingly, a PoC device needs to be calibrated with respect to a particular analyte in order to measure the energy properties thereof. Therefore, in some embodiments, the PoC device for measuring multiple analyte may comprise a calibration functionality for adjusting the settings thereof for adapting to each of the multiple analyte.

In some embodiments, one or more potentiostat circuitries may be calibrated by using diluted human plasma/serum/blood/fluid samples with known concentrations of targeted disease-analyte (such as but not limited to N-terminal Pro B-type natriuretic peptide (NT-pro-BNP), troponin, ck-mb, D-dimer, creatinine, electrolytes), obtained anonymously from suitable sources such as medical labs. The potentiostat circuitries of the PoC device may then be calibrated using samples of different analyte concentrations.

In some embodiments, the PoC device uses an identification element on the electrochemical-sensor structure or on the carrying vial thereof for determining the biomarker to be analyzed. The identification element may include detection electrodes, radio frequency identification (RFID) tags, one-dimensional barcodes, two-dimensional barcodes such as Quick Response (QR) codes, and/or the like.

In some embodiments, the portable electrochemical-sensor system may be configured for monitoring heart failure (HF) by detecting and quantifying HF-related analytes such as NT-pro-BNP, Cardiac troponin (cTn), and/or the like from a small volume of bodily fluid samples such as a blood sample obtained through a simple sampling process such as finger pricking.

cTn is a highly sensitive and specific biomarker of myocardial injury. cTn guides triage and management of patients presenting with symptoms suggestive of acute coronary syndrome. On the other hand, B-type natriuretic peptide (BNP) level is also elevated in acute myocardial infarction and is a quantitative biochemical marker related to the extent of infarction and the left ventricle systolic dysfunction. Thus, BNP has prognostic value. The most potent inducer of BNP gene transcription is left ventricular (LV) wall stretch from increased pressure or volume. A prohormone (proBNP) is cleaved to BNP and NT-pro-BNP, resulting in a serologic evidence of BNP, NT-pro-BNP, and proBNP. Conventional assays for BNP detect proBNP and BNP, as well as various degraded fragments of BNP, while NT-pro-BNP assays detect NT-pro-BNP and proBNP. While BNP and NT-pro-BNP are passively cleared by a number of organs including kidneys, the half-life of BNP is significantly shorter than that of NT-pro-BNP (e.g., approximately 20 minutes vs. 60 to 120 minutes). Therefore, NT-pro-BNP is considered a very promising candidate biomarker in the applications for prognosis of heart failure at home or in ambulatory environments.

Detection of analyte binding signal can be based on electrochemical signals, optical signals (such as chemiluminescence, reflectance, and/or the like), or magnetic transduction signals. Such electrochemical detection methods rely on either voltage or current to detect analyte binding and are suitable for implementation in miniaturized electrical biosensor devices. These methods monitor the change in electrical impedance that occurs when an analyte binds to the capture ligand which is then correlated to the concentration of the target analyte.

A main challenge of electrochemical detection and quantification of HF biomarkers (e.g., NT-pro-BNP, cTn, and/or the like) is their low concentration in blood and thus the amplitude of their biomolecular binding events (Cut-off value: less than 0.125 nanograms per milliliter (ng/mL)= Exclusion of Non-acute heart failure).

In order to amplify the biomolecular binding signal, a method utilizing nanostructured sensing surfaces may be used for achieving improved sensitivity (such as less than or equal to 1 ng/mL). The sensing surfaces have nanoscale dimensions matching in size with the targeted troponin molecules with increased surface-area-to-volume ratio and structural morphology for providing selective functionalization sites for analyte binding with its corresponding capture ligand.

Description of Various Embodiments

Figure 1B:
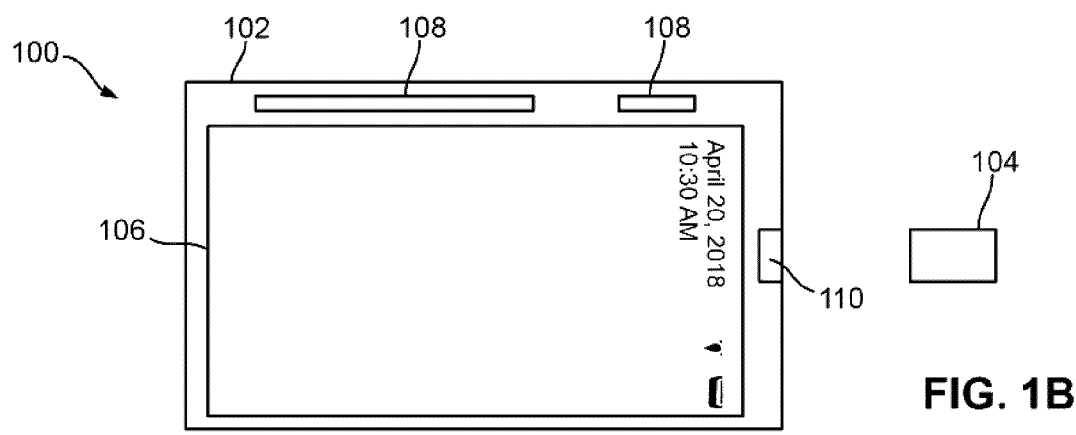

Turning now to FIGS. 1A and 1B, an electrochemical-sensor system for monitoring a user's health conditions is shown and is generally identified using the reference numeral 100. The portable electrochemical-sensor system 100 comprises a diagnostic apparatus 102 and a sampling structure 104 such as a disposable electrochemical-sensor structure.

In these embodiments, the diagnostic apparatus 102 may be a portable PoC device such as a Philos™ PoC device (Philos is a trademark of CardiAI Technologies Ltd. of Calgary, Alberta, Canada) and has a size suitable for personal use (e.g. a size of 5 centimeters (cm)×7.5 cm×2 cm in one embodiment). The PoC device 102 in these embodiments comprises a screen 106, a user-input structure for receiving user inputs, a strip-receiving port 110 for receiving the electrochemical-sensor structure 104, a control structure (not shown) such as a RFduino microcontroller offered by RFduino Inc. of Hermosa Beach, CA, USA, and relevant circuitries. The PoC device 102 also comprises a power source such as battery for powering various components.

The user-input structure may comprise one or more buttons 108 and/or a touch-sensitive screen (such as a touch-sensitive screen 106 in some embodiments) for receiving user inputs such as user instructions (e.g., turning the PoC device 102 on or off, starting a diagnostic process, displaying readings obtained in the diagnostic process, displaying previous diagnostic readings, and/or the like) and/or user data (e.g., the user's age, sex, weight, height, and/or the like).

The circuitries may include an analysis circuitry such as a potentiostat circuitry for bio-sensing (described in more detail later) and a monitoring circuitry for other tasks such as performing user-instructed operations, detecting the insertion of the electrochemical-sensor structure 104, reading and displaying the measured levels of biomarkers, storing measurement data, transmitting measurement data to a remote device for trend tracking, and/or the like. The potentiostat circuitry may be designed corresponding to the circuitry of the electrochemical-sensor structure 104.

Figure 2:
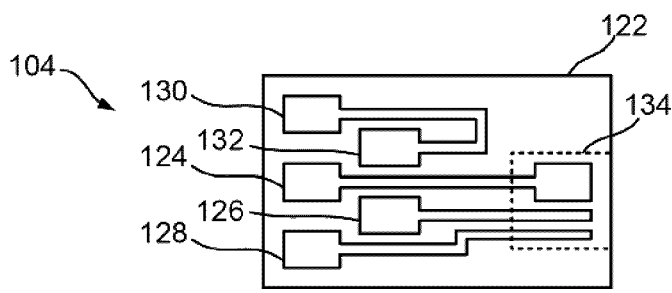
FIG. 2 is a schematic plan view of the electrochemical-sensor structure of the health monitoring system shown in FIG. 1A, the electrochemical-sensor structure comprising a plurality of electrodes.

As shown in FIG. 2, the electrochemical-sensor structure 104 may comprise a plurality of electrodes 124 to 132 distributed on a biocompatible substrate 122 that enables fluid to flow thereon. Parameters related to the substrate's effective conductance and/or impedance may be used to reveal or derive characteristic information about a single entity, or an interaction between two or more entities. The entity includes but is not limited to a monolayer, a stack of monolayers, proteins, oligonucleotides, enzymes, or any combination thereof.

In particular, the electrochemical-sensor structure 104 in this embodiment comprises a reference electrode (RE) 124, a control electrode (CE) 126, and a working electrode (WE) 128, all extending into a sampling region 134 thereof for measuring the energy properties of a bodily fluid sample (not shown) received therein. The surfaces of the electrodes may be modified or otherwise treated with a mediator to mediate the electron transfer from the electrodes to body fluids.

The electrochemical-sensor structure 104 also comprises a pair of identification electrodes 130 and 132 joined by a trace with a pre-defined resistance or a pre-defined impedance for indicating the type of biomarker that the electrochemical-sensor structure 104 is suitable to detect. The electrodes 124 to 132 may be made of or comprise conductive or semi-conductive metals such as gold (Au), chromium (Cr), titanium, platinum, silver, and/or the like.

With such an electrochemical-sensor structure 104, the analysis circuitry correspondingly comprises a set of coupling electrodes in the strip-receiving port 110 for electrically engaging the electrodes 124 to 132 of the electrochemical-sensor structure 104.

Figure 3A:
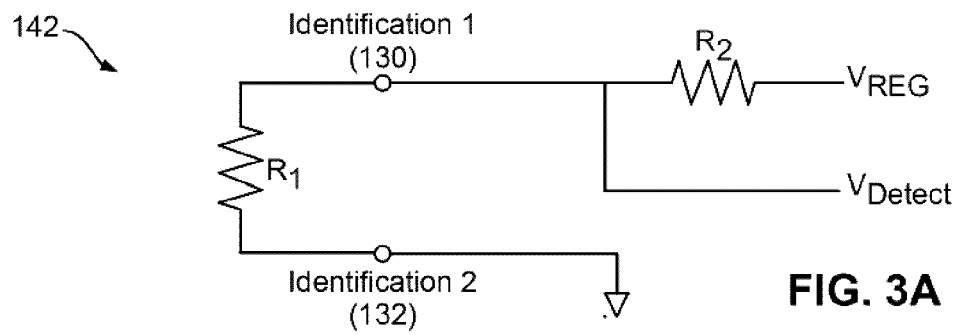
FIGS. 3A and 3B are schematic diagrams of the circuitries of the PoC device shown in FIG. 2 for electrically coupling to the electrodes of the electrochemical-sensor structure for measuring one or more biomarkers in the bodily fluid sample on the electrochemical-sensor structure.
Figure 3B:
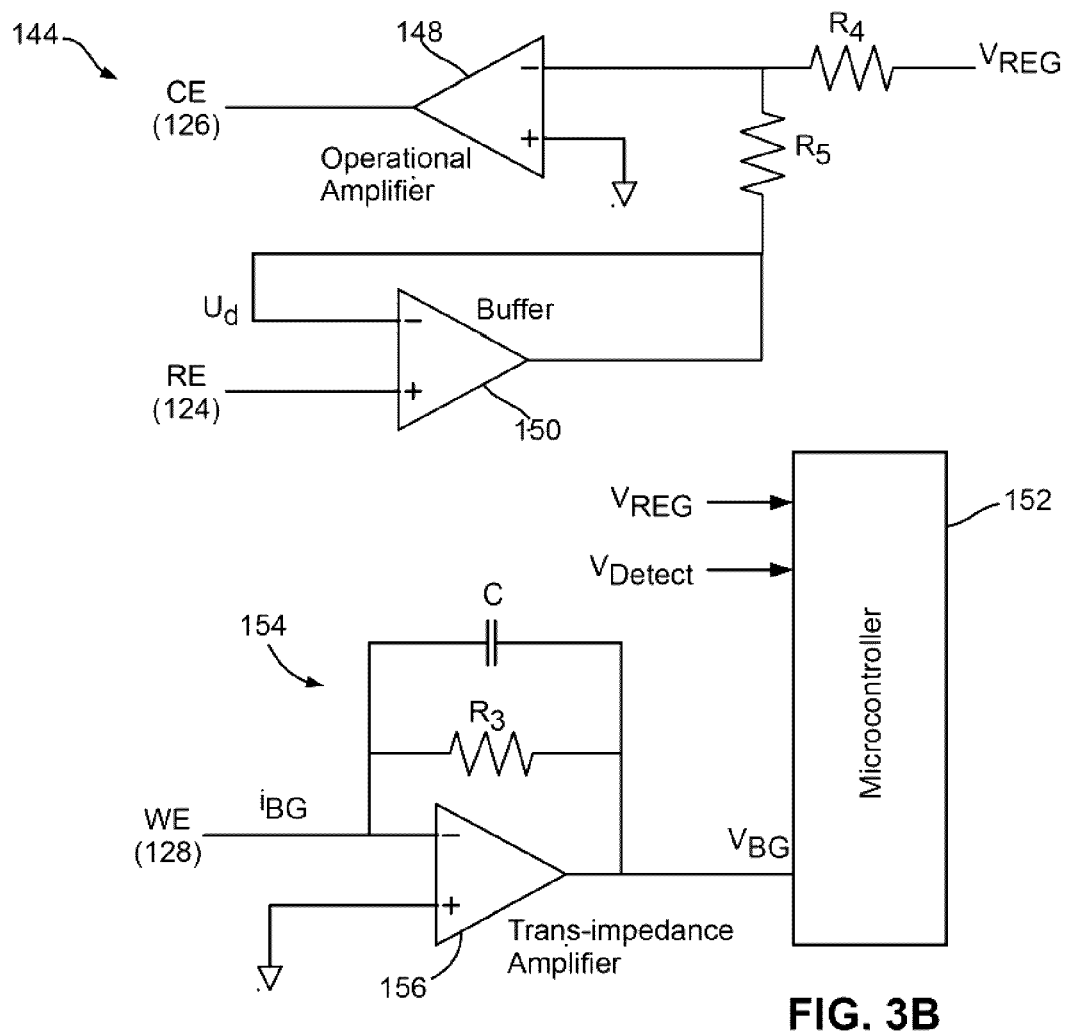

As shown in FIGS. 3A and 3B, the PoC device 102 comprises a plurality of circuitries 142 and 144 for electrically engaging the electrodes 124 to 132 when the electrochemical-sensor structure 104 is inserted into the strip-receiving port 110.

As shown in FIG. 3A, a first circuitry 142 in the form of a voltage divider is used for determining the type of the biomarker. As described above, the identification electrodes 130 and 132 have a pre-defined resistance therebetween which is represented by a resistor $R_1$. The resistance of $R_1$ is predefined and indicative of the type of biomarker that the electrochemical-sensor structure 104 is suitable to detect. The second circuitry 144 electrically engages the identification electrodes 130 and 132 and applies a voltage $V_{REG}$ (e.g., 3.3V) thereto via a resistor $R_2$ with known resistance. A voltage signal $V_{Detect}$ is outputted from between $R_1$ and $R_2$. Therefore, $V_{Detect} = V_{REG} R_1/(R_1+R_2)$, and the resistance of $R_1$ and in turn the type of the biomarker may be obtained by comparing $V_{Detect}$ with $V_{REG}$.

As shown in FIG. 3B, a second circuitry 144 in the form of a Direct-Current (DC) potentiostat circuitry is used to control the voltage between the WE 128 and RE 124. Herein, the bodily fluid sample on the electrochemical-sensor structure 104 acts as the electrolyte between the WE 128 (acting as a cathode), the RE 124 (acting as an anode), and the CE 126. Because of the nature of the operational amplifier 148, a current is supplied through the CE 126 until the voltage at RE 124 and $U_d$ is the same. Thus, $U_d$ determines the voltage of the electrolyte, and consequently determines the accuracy of biomarker measurements as a too-low $U_d$ may not be able to generate a sufficient measurement resolution and a too-high $U_d$ may trigger inferencing reactions or surface property changes.

Thus, in the circuitry 144, the three-electrode configuration is connected to a DC potentiostat circuitry wherein a constant DC voltage is regulated and applied over the WE 128 and RE 124 of the electrochemical-sensor structure 104. The circuitry 144 may be used for determining the energy properties of a sample fluid for analysis of the sample fluid by detecting and determining impedimetric measurements. Those skilled in the art will appreciate that the circuitry 144 may also be used for the amperometric type of measurements which is commonly used in glucose detection. Moreover, the potentiometric type of measurements may also be implemented using the three-electrode configuration, wherein an Alternate-Current (AC) wave with a predefined frequency is applied for stimulating the bodily fluid sample while forward (e.g. by increasing the voltage) and reverse (e.g. by decreasing the voltage) current is measured to yield a differential current (forward-reverse).

As shown in FIG. 3B, a control structure 152 (e.g., a microcontroller) compares $V_{Detect}$ with $V_{REG}$ and determines the type of the biomarker. The microcontroller 152 then adjusts the bio-sensing parameters (such as $U_d$) to adapt to the determined type of the biomarker and measures the voltage of WE 128. An amplifying circuitry 154 which in this embodiment comprises an amplifier 156, a resistor $R_3$, and a capacitor C is used to amplify the signal of WE 128. In this way, the energy properties of the biomarker in the bodily fluid sample on the electrochemical-sensor structure 104 are measured and are used for determining the patient's health conditions.

While $U_d$ and the voltage of the electrolyte determine the accuracy of biomarker measurements, the physical and electrochemical structures of the electrochemical-sensor structure 104 also determine the accuracy of biomarker measurements. Moreover, the physical and electrochemical structures of the electrochemical-sensor structure 104 also determine other necessary features thereof such as dust prevention, electrode robustness, ease-of-use, cost-of-manufacturing, and the like.

FIGS. 4A to 4D show the physical and electrochemical structures of the electrochemical-sensor structure 104 in some embodiments. As shown, the electrochemical-sensor structure 104 comprises a substrate 122 with electrodes 124 to 132 deposited, printed, or otherwise coupled thereto on a same side thereof. As those skilled in the art will appreciate, situating all electrodes 124 to 132 on the same side of the electrochemical-sensor structure 104 facilitates the miniaturization of the electrochemical-sensor structure 104, thereby providing an elegant connector design, ease of user handling, and ease of sampling bodily fluid.

Figure 4A:
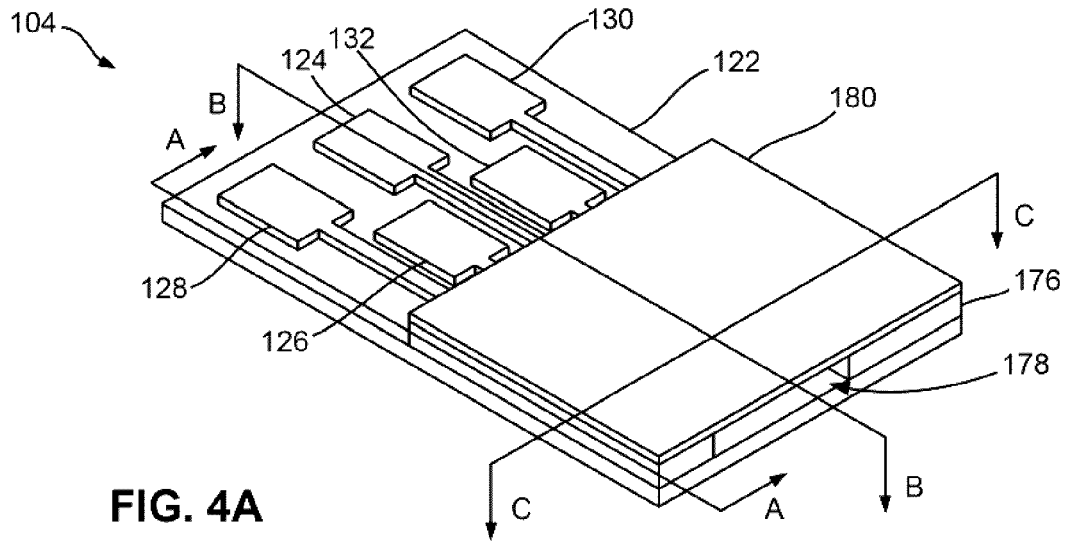
FIG. 4A is a perspective view of the electrochemical-sensor structure of the health monitoring system shown in FIG. 1A.
Figure 4B:
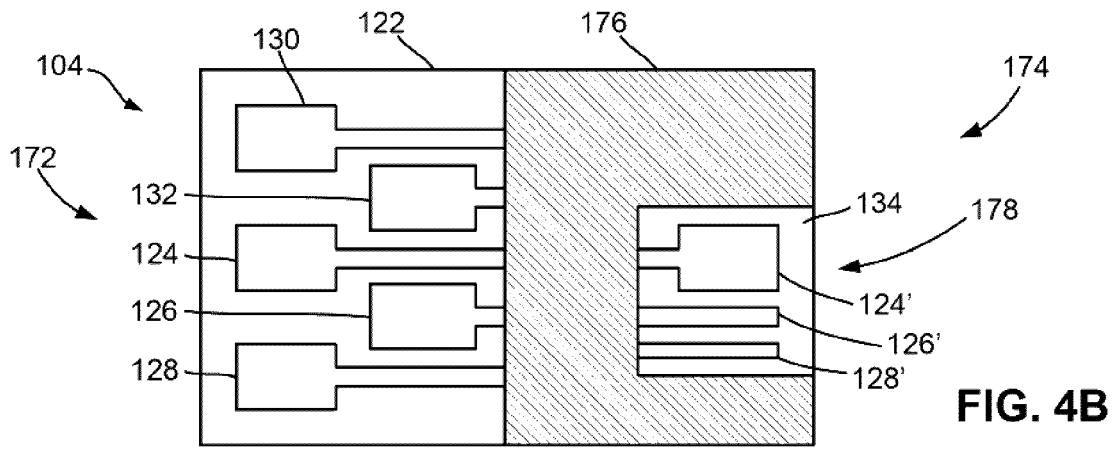
FIG. 4B is a cross-sectional view of the electrochemical-sensor structure shown in FIG. 4A along the cross-sectional line A-A.
Figure 4C:
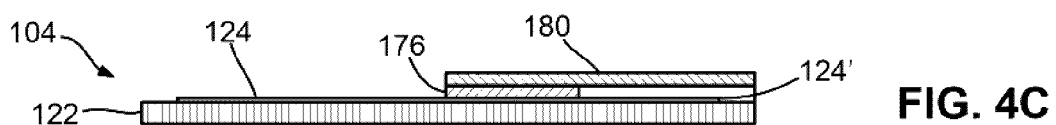
FIG. 4C is a cross-sectional view of the electrochemical-sensor structure shown in FIG. 4A along the cross-sectional line B-B.
Figure 4D:
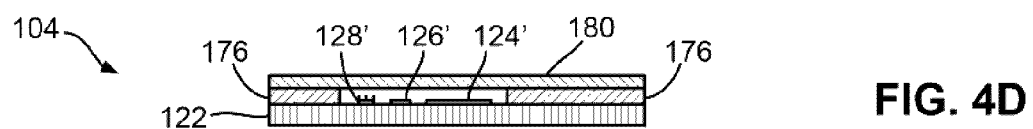
FIG. 4D is a cross-sectional view of the electrochemical-sensor structure shown in FIG. 4A along the cross-sectional line C-C.

The identification electrodes 130 and 132 are located about a proximal end 172 of the electrochemical-sensor structure 104 (which is the end thereof for inserting into the strip-receiving port 110 of the PoC device 102) and are electrically connected with the predefined resistance $R_1$. The electrodes RE 124, CE 126, and WE 128 extend from the proximal end 172 of the electrochemical-sensor structure 104 to a distal end 174 thereof. As shown in FIG. 4B, the distal-side electrodes RE 124', CE 126', and WE 128' (corresponding to and connected to the RE 124, CE 126, and WE 128, respectively) are laterally spaced at a same distance. The electrode RE 124' has a much larger surface than that of the electrode CE 126' or WE 128'. For example, in some embodiments, the surface-area ratio of WE 128', CE 126', and RE 124' may be about 1:1:4.

the electrochemical-sensor structure 104 in these embodiments also comprises a hydrophobic middle layer 176 covering a distal portion (also identified using reference numeral 174) of the electrochemical-sensor structure 104 except at the sampling region 134 about the distal-side electrodes RE 124', CE 126', and WE 128'. The hydrophobic middle layer 176 has a distal-end opening 178 forming a rear-facing sampling port (also identified using reference numeral 178) for receiving a bodily fluid sample into the sampling region 134 and in contact with the distal-side electrodes RE 124', CE 126', and WE 128'. The electrochemical-sensor structure 104 further comprises a protection layer 180 on top of the hydrophobic middle layer 176 and covering the distal portion 174 (including the sampling region 134). In these embodiments, the protection layer 180 is made of a suitable material such as glass or plastic.

In some embodiments, the substrate 122 may be made of a flexible material such as a flexible polyimide membrane strip with one or more detection elements thereon for detecting one or more biomarkers. In some embodiments, the flexible substrate 122 may be made of a modified or unmodified polymeric substrate including but not limited to track-etched membranes, treated or untreated acrylic substrates, and/or the like. In some embodiments, the track-etched membrane 122 may be a porous polyimide membrane.

In some embodiments, the track-etched membrane 122 may have a porosity equal to or greater than 30%. Herein, the porosity of a material is defined as the ratio of the volume of void or empty spaces over the total volume of the material. In some embodiments, the track-etched membrane 122 may have a porosity equal to or greater than 50%.

In some embodiments, pore size, shape, and density of the track-etched membrane can be varied in a controllable manner so that a membrane with selected transport and retention characteristics can be produced. Because of the precisely determined structure of track-etched membranes, using a track-etched membrane as the substrate 122 may give rise to distinct advantages over conventional membranes. For example, in some embodiments, pore size, shape, and density of the track-etched membrane 122 may be varied in a controllable manner so that a membrane with selected transport and retention characteristics may be produced. A membrane 122 with a higher pore density allows the metal layers to be coupled thereto with coarser surfaces which in turn allows increased capacity to house a larger amount metal layers of three-dimensional (3D) nano-rods (described later) to be grown at the membrane surface. More nano-rods relate to more binding sites available for antibody molecules, which in turn increases the overall sensitivity of the electrochemical-sensor structure 104. Moreover, a membrane 122 with a higher pore density also facilitates the flow of the bodily fluid sample thereon.

Figure 5A:
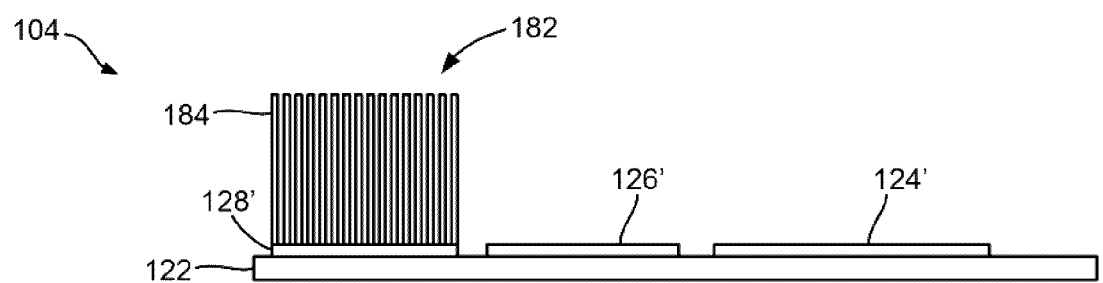
FIG. 5A is a schematic view of the electrochemical-sensor structure shown in FIG. 4A having a substrate and a plurality of electrodes including a reference electrode (RE), a control electrode (CE), and a working electrode.
Figure 5B:
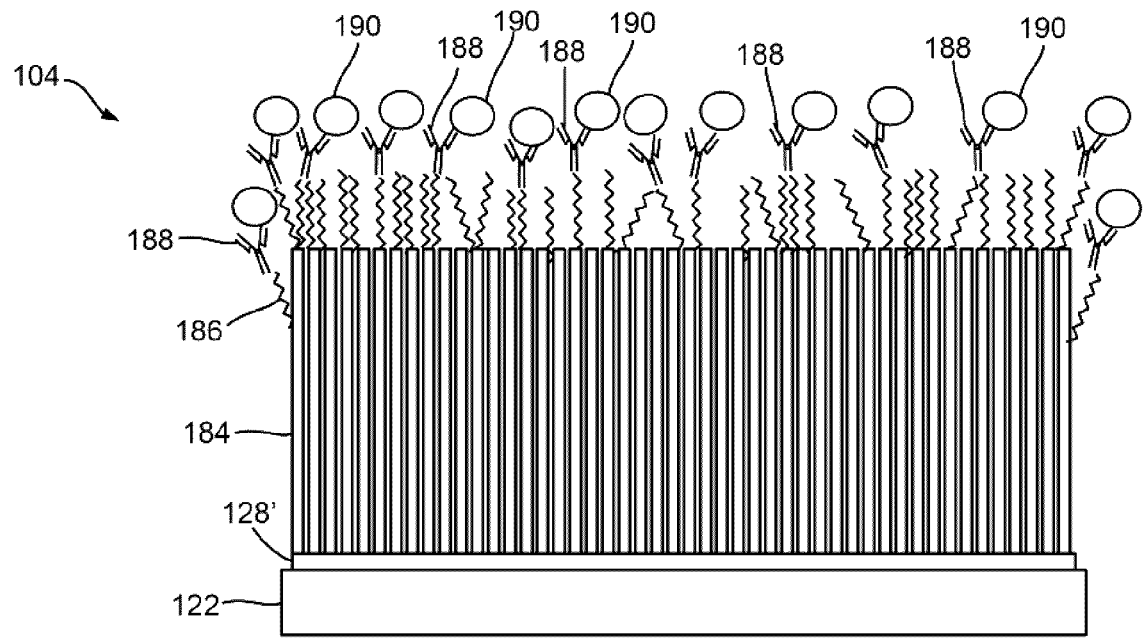
FIG. 5B is a schematic view of the electrochemical-sensor structure shown in FIG. 4A, illustrating the substrate and the WE, wherein the WE comprises a nanostructured-sensing surface having ZnO nano-rods.

FIG. 5A is a schematic view of the electrochemical-sensor structure 104 showing the substrate 122 and the electrodes RE 124', CE 126', and WE 128'. FIG. 5B is a schematic view of the electrochemical-sensor structure 104 showing the substrate 122 and the electrode WE 128'. As shown, the electrochemical-sensor structure 104 comprises a nanostructured-sensing surface in the sampling region 134 thereof for amplifying the amount of biomarker binding to the electrochemical-sensor structure 104 in order to achieve improved sensitivity.

More specifically, the distal-side electrode WE 128' comprises a nanostructured-sensing surface 182 having a plurality of nano-rods 184 such as Zinc-Oxide (ZnO) nano-rods. In some embodiments, the ZnO nano-rods may be synthesized by depositing ZnO onto the distal-side electrode WE 128' on the substrate (acting as seeds) and then immersing the substrate consisting the coated electrode in a chemical bath consisting of zinc nitrate hexahydrate and hexamethyline tetramine at a temperature below the boiling point of water and preferably about 80° C. for "growing" the ZnO nano-rods.

The nano-rods 184 are coated with a specific type of detection element 188 such as one or more immobilized capture ligand such as antibodies, enzymes, nucleic acid aptamers, and the like, for detecting a specific biomarker 190 for which the detection element 188 has a high specificity and affinity. The nano-rods 184 are also coated with crosslinking molecules 186 which immobilize the detection-element molecules 188 onto the nano-rods 184 for capturing and reacting with the corresponding biomarkers 190.

FIGS. 6A to 6F illustrate a process for manufacturing the electrochemical-sensor structure 104 having ZnO nano-rods in these embodiments.

Figure 6A:
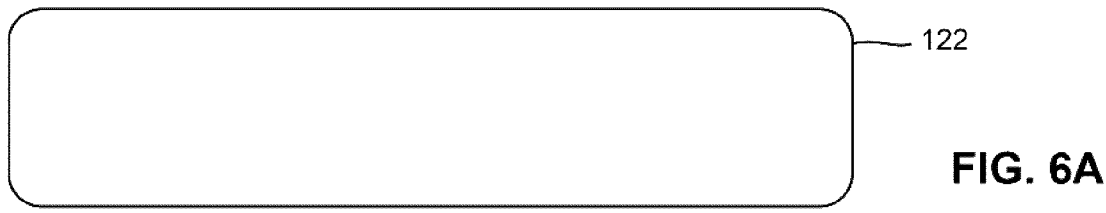
FIGS. 6A to 6F show a process for manufacturing the electrochemical-sensor structure having ZnO nano-rods.

As shown in FIG. 6A, a track-etched porous polyimide membrane of about 25 μm thickness is prepared as the substrate 122.

Figure 6B:
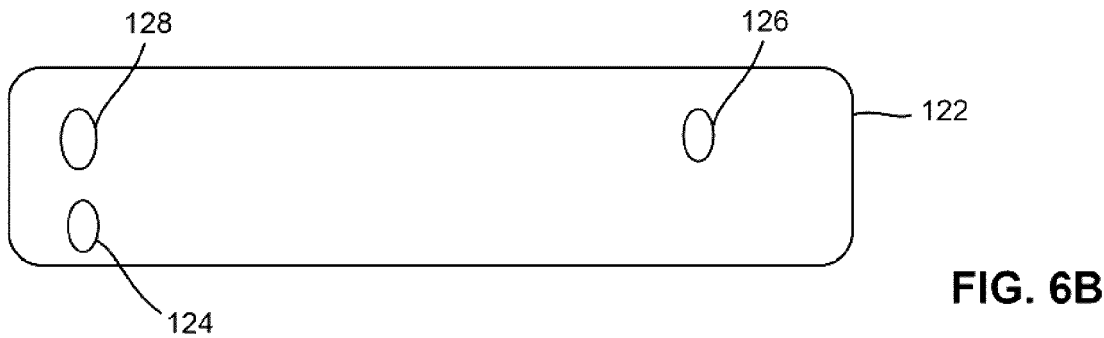

As shown in FIG. 6B, a patterned stencil mask with exposures of a 50-millimeter (mm) diameter is applied to the substrate 122 at the locations of the electrodes RE 124, CE 126, and WE 128. Then sputter-coating or E-beam coating is used to deposit 25 nanometer (nm) Cr and 125 nm Au at the electrode locations to form the electrodes RE 124, CE 126, and WE 128.

Figure 6C:
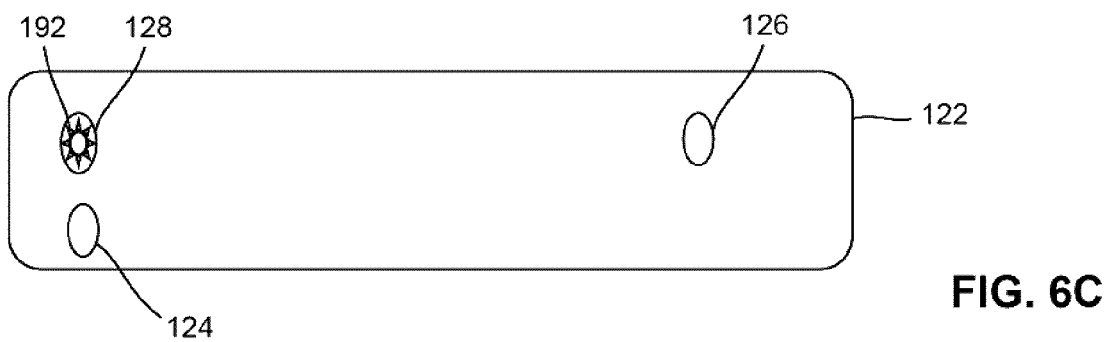

As shown in FIG. 6C, a secondary stencil mask with a 50 mm-diameter exposure at the location of the electrode WE 128 is applied to the substrate 122 and a ZnO seed-layer 192 is selectively deposited onto the electrode WE 128 in conventional RF-magnetron sputter using ZnO of a 99.99% purity under 12 standard cubic centimeters per minute (sccm) Argon (Ar) plasma with no oxygen and with power at 50 Watts (W). The deposition is then carried at a base pressure of 15 millitorr (mTorr) for about 30 minutes.

The thickness of the deposited ZnO seed-layer is about 30±5 nm which may be validated using a suitable profilometer such as a Dektak 8 profilometer offered by Veeco Instruments Inc. of Plainview, New York, USA.

Figure 6D:
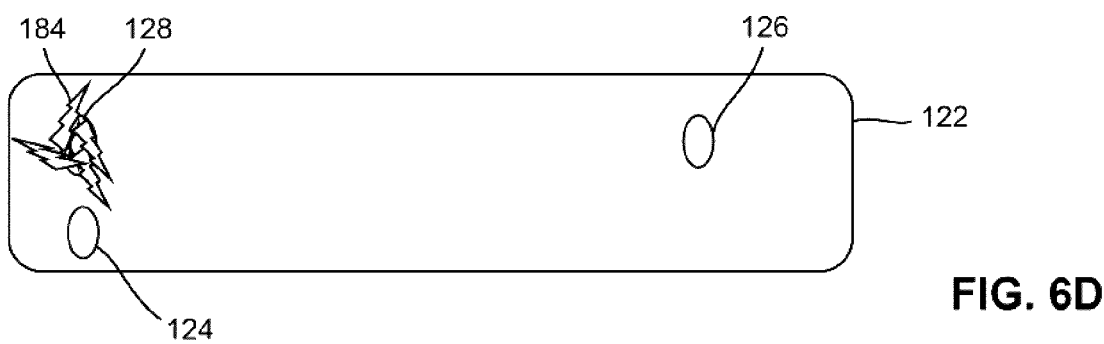

As shown in FIG. 6D, ZnO nano-rods are then synthesized on the electrode WE 128 using a suitable hydrothermal method, e.g., by immersing the electrodes-formed substrate 112 in a chemical bath consisting of zinc nitrate hexahydrate $(Zn(NO_3)_2)$ with an equimolar concentration of 50 millimolar (mM) and hexamethyline tetramine (HMTA) for nucleation at a temperature of about 80° C. and 300 revolutions per minutes (rpm) for 30 minutes, for "growing" the ZnO nano-rods 184. Then, the processed substrate 112 is rinsed with deionized water and air dried.

Figure 6E:
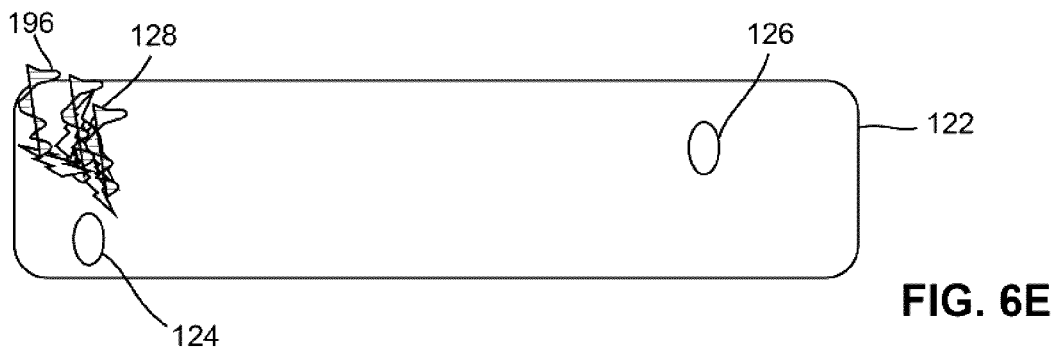
Figure 6F:
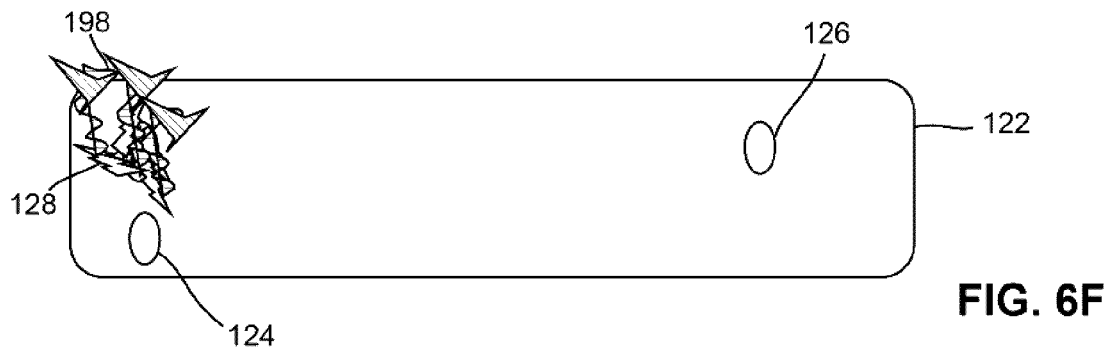

As shown in FIGS. 6E and 6F, immobilization of protein onto the electrode WE 128 is conducted by first using 10 mM dithiobis(succinimidyl propionate) (i.e., DSP) 196 in dimethyl sulfoxide (i.e., DMSO) for 2 hours, and then using a one (1) microgram per milliliter (μg/mL) anti-NT-pro-BNP antibody 198 in phosphate-buffered saline (PBS) for 15 minutes. Unbound DSP is blocked by a suitable protein-blocking buffer such as the Thermo Scientific SuperBlock™ Blocking Buffer (SuperBlock is a trademark of Thermo Fisher Scientific Inc. of Waltham, Massachusetts, USA).

The electrochemical-sensor structure 104 having ZnO nano-rods is then made.

In some embodiments, the metal-oxide nanostructures may be synthesized by depositing metal-oxide onto the one or more WE electrodes via an electrochemical process.

FIGS. 7A to 7E illustrate a process for manufacturing the electrochemical-sensor structure 104, according to some alternative embodiments of this disclosure. In these embodiments, the ZnO nano-rods are not used. Instead, a highly conductive nano-material 206 such as carbon nano-tubes, nano-size gold particles, and/or the like is applied onto the distal-side electrode WE 128' for forming the biosensor with increased surface area and therefore improved sensitivity.

Figure 7A:
FIGS. 7A to 7E illustrate a process for manufacturing the electrochemical-sensor structure shown in FIG. 4A, according to some embodiments of this disclosure.

As shown in FIG. 7A, the substrate 122 is first prepared. In this example, the substrate is made of or comprises Poly(methyl methacrylate) (i.e., PMMA) and track-etched polyamide, polyester, and/or polycarbonate.

PMMA is a clear thermoplastic. Compared to other materials such as polycarbonate, PMMA has a higher transmissivity, a higher ultra-violet (UV) resistance (therefore not turning yellow over time), and a higher rigidity (thus a higher scratch-resistance). PMMA is suitable for smooth laser-cut without becoming yellow and burnt during laser cut, and may be remolded and recycled without degradation. As a comparison, polycarbonate may easily become yellow and burnt during laser cut. PMMA is also easier to polish (e.g., to make smooth edges for injury prevention). Moreover, PMMA is cost-effective compared to other materials such as polycarbonate.

Figure 7B:
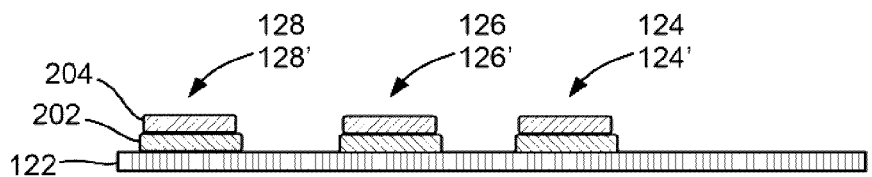

As shown in FIG. 7B, the electrodes WE 128/128', CE 126/126', and RE 124/124' are formed on the substrate 122 by depositing a layer of Cr 202 onto the substrate 122 and a layer of Au 204 onto the Cr layer 202 using a suitable deposition method such as Chemical Vapor Deposition (CVD), Plasma Vapor Deposition (PVD), sputter coating, E-beam, or the like, with a first mask applied on to the substrate 122 which only exposes the locations of the electrodes.

Although not shown, other electrodes such as the identification electrodes 130 and 132 may also be formed at this step.

After electrode deposition, Scanning Electron Microscopy (SEM) and/or Atomic Force Microscopy (AFM) may be used for characterization tests of the deposited electrodes.

Figure 7C:
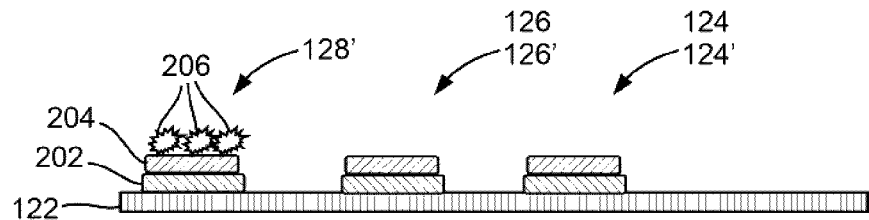

As shown in FIG. 7C, the WE 128/128' is functionalized by applying a layer of conductive nano-material 206 onto the Au layer 204 for forming the biosensor with increased surface area and therefore improved sensitivity. At this step, a suitable deposition method such as CVD, PVD, sputter coating, E-beam, or the like, may be used with a second mask applied on to the electrode-deposited substrate 122 which only exposes the distal-side electrode WE 128'.

Characterization tests of the nano-material layer 206 may be conducted by using SEM, Energy Dispersive X-Ray Analyzer (EDX), transmission electron microscope (TEM), AFM, and/or the like.

Figure 7D:
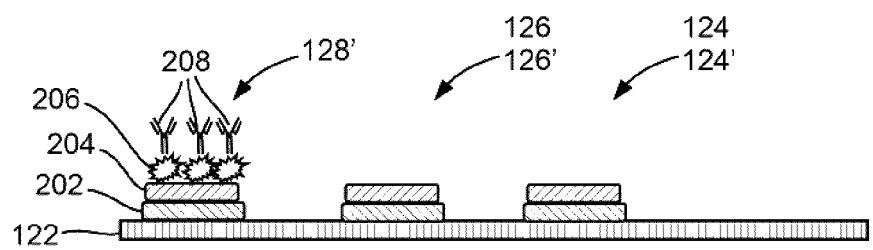

As shown in FIG. 7D, immunoglobulins or antibodies 208 are immobilized onto the nano-material layer 206 of the WE 128' forming a layer of detection element, and optimization of the antibody concentration and interaction time between antibody and antigen is conducted. Then, characterization tests may be conducted by using SEM and/or AFM.

Figure 7E:
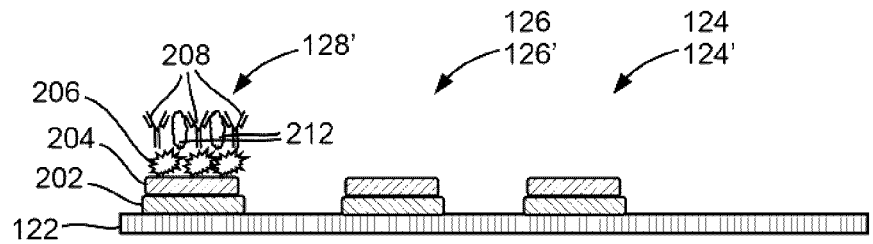

As shown in FIG. 7E, a suitable biomaterial or blocking agent 212 is coated to the antibodies 208.

Then, the hydrophobic middle layer 176 is applied about the electrodes 124', 126', and 128' and forming the sampling region 134. The manufacturing of the electrochemical-sensor structure 104 is completed after the protection layer 180 is coupled to the hydrophobic middle layer 176.

In these embodiments, the substrate 112 is made of a non-porous PMMA membrane. However, the highly conductive nanocomposite deposited thereon provide sufficient binding sites available for antibody molecules, compared to the track-etched, porous membranes.

Those skilled in the art will appreciate that other suitable materials such as polyethylene terephthalate (PET) may be used for making the substrate 112 in other embodiments.

In above embodiments, the electrochemical-sensor structure 104 comprises the identification electrodes 130 and 132 for indicating the type of the biomarker associated therewith. When an electrochemical-sensor structure 104 is inserted or otherwise coupled to the PoC device 102, the PoC device 102 checks the type of the biomarker associated with the inserted electrochemical-sensor structure 104. If the PoC device 102 determines that the electrochemical-sensor structure 104 is not compatible therewith, the PoC device 102 may present an alarm or warning (e.g., a beep and/or a warning on the screen 106).

Figure 8:
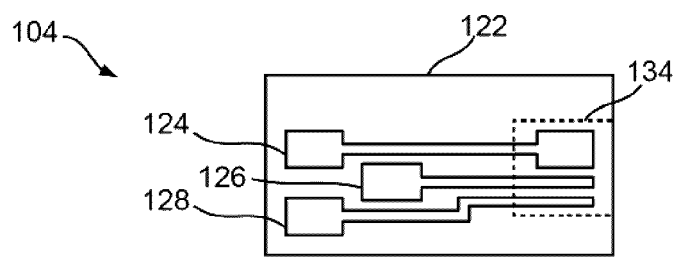
FIG. 8 is a schematic plan view of the electrochemical-sensor structure of the health monitoring system shown in FIG. 1A, according to some embodiments of this disclosure.

In some alternative embodiments as shown in FIG. 8, the electrochemical-sensor structure 104 does not comprise any identification electrodes. In the example shown in FIG. 8, the electrochemical-sensor structure 104 only comprises three electrodes RE 124, CE 126, and WE 128. In these embodiments, the portable electrochemical-sensor system 100 may use other suitable methods for determining the type of biomarker that the electrochemical-sensor structure 104 is suitable to detect, as described below.

Figure 9A:
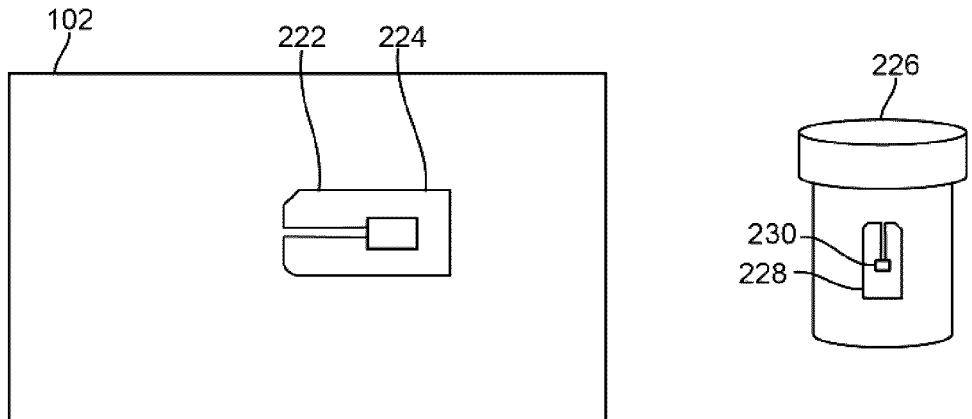
FIG. 9A shows a PoC device having a radio frequency identification (RFID) reader and a carrying vial having a RFID tag, according to some embodiments of this disclosure, the PoC device determining the type of biomarker associated with the electrochemical-sensor structures in the carrying vial by reading the information of the RFID tag of the carrying vial.

For example, in one embodiment as shown in FIG. 9A, the PoC device 102 comprises a RFID tag antenna 222 and a RFID reader 224 built into the back of the device. Correspondingly, the carrying vial 226 (also called a strip vial) that accommodates the electrochemical-sensor structures 104 comprises a RFID tag antenna 228 and a RFID chip 230 storing information of the type of the biomarker associated with the electrochemical-sensor structures 104 in the strip vial 226. The PoC device 102 may use the RFID reader 224 to read the information in the RFID chip 230 of the strip vial 226 to determine the type of biomarker being that the electrochemical-sensor structures 104 can detect.

Each time before a patient begins to do a new test, the PoC device 102 may ask the patient to place the carrying vial 226 into the vicinity of PoC device 102 for obtaining the identification information of the electrochemical-sensor structure 104. Based on the information received by the RFID reader in the PoC device 102, the PoC device 102 determines whether or not the electrochemical-sensor structure 104 is compatible therewith (i.e., whether or not the PoC device 102 and the electrochemical-sensor structure 104 are for detecting the same biomarker). If the PoC device 102 determines that the electrochemical-sensor structures 104 in the strip vial 226 are not compatible, the PoC device 102 may present an alarm or warning (e.g., a beep and/or a warning on the screen 106).

In some embodiments, instead of presenting an alarm or warning, the PoC device 102 may adjust the electrical parameters of the potentiostat circuitry based on the information detected from the strip vial 226 to adapt to the type of electrochemical-sensor structure 104 contained in the strip vial 226 for accurate biomarker detection.

In another embodiment, each electrochemical-sensor structure 104 may comprise a RFID chip storing information of the type of the biomarker associated therewith. If the PoC device 102 determines that the electrochemical-sensor structure 104 is not compatible, the PoC device 102 may present an alarm or warning (e.g., a beep and/or a warning on the screen 106). Alternatively, the PoC device 102 may adjust the electrical parameters of the potentiostat circuitry thereof based on the information detected from the electrochemical-sensor structure 104 to adapt thereto for accurate biomarker detection.

Figure 9B:
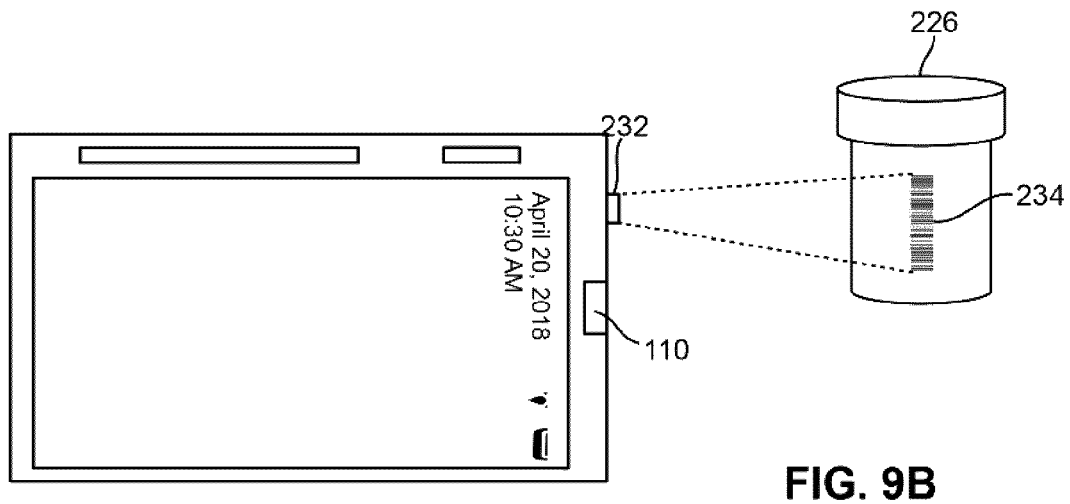
FIG. 9B shows a PoC device having a one-dimensional barcode scanner and a carrying vial having a one-dimensional barcode, according to some embodiments of this disclosure, the PoC device determining the type of biomarker associated with the electrochemical-sensor structures in the carrying vial by reading the information of the one-dimensional barcode of the carrying vial.

In one embodiment as shown in FIG. 9B, the PoC device 102 comprises an imaging component 232 such as a one-dimensional barcode scanner for scanning a one-dimensional barcode. Correspondingly, the strip vial 226 comprises a one-dimensional barcode 234 storing, encoding, or otherwise indicative of the identity or type of the biomarker associated with and analyzable by using the electrochemical-sensor structures 104 in the strip vial 226.

The PoC device 102 may use the barcode scanner 232 to read the one-dimensional barcode 234 on the strip vial 226 to determine the type of biomarker analyzable by using the electrochemical-sensor structures 104. If the PoC device 102 determines that the electrochemical-sensor structures 104 in the strip vial 226 are not compatible, the PoC device 102 may present an alarm or warning (e.g., a beep and/or a warning on the screen 106) or adjusting the electrical parameters of the potentiostat circuitry as described above.

In another embodiment, each electrochemical-sensor structure 104 may comprise a one-dimensional barcode (e.g., on the "bottom" side thereof opposite to the sampling region 134) indicative of the type of the biomarker associated therewith.

In one embodiment, the PoC device 102 comprises a scanner or imaging component for scanning a matrix barcode or two-dimensional barcode such as a QR-code. Correspondingly, the strip vial 226 comprises a QR-code indicative of the type of the biomarker associated with the electrochemical-sensor structures 104 in the strip vial 226. The PoC device 102 may use the QR-code scanner to read the QR-code on the strip vial 226 to determine the type of biomarker being that the electrochemical-sensor structures 104 can detect. If the PoC device 102 determines that the electrochemical-sensor structures 104 in the strip vial 226 are not compatible, the PoC device 102 may present an alarm or warning (e.g., a beep and/or a warning on the screen 106) or adjusting the electrical parameters of the potentiostat circuitry as described above.

In another embodiment, each electrochemical-sensor structure 104 may comprise a QR-code (e.g., on the back thereof) indicative of the type of the biomarker associated therewith.

In some embodiments, the PoC device may have an infrared scanner and may recognize the type of electrochemical-sensor structure 104 inserted into its strip-receiving port 110 by use of the infrared scanner to read a one-dimensional barcode or QR-code located on the carrying vial in which the electrochemical-sensor structures 104 are stored.

Figure 10:
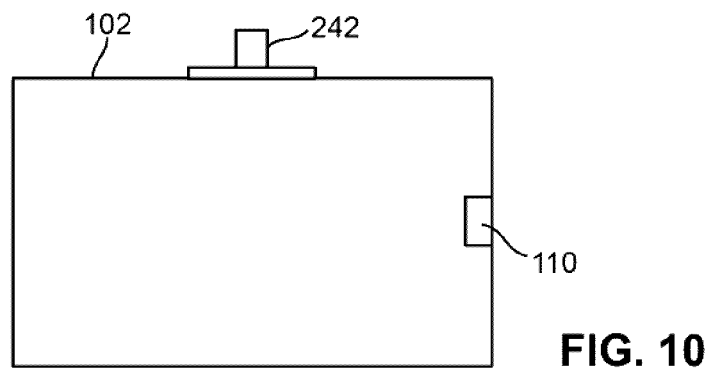
FIG. 10 shows a PoC device having a connection port for physically and electrically coupling to a smartphone, according to some embodiments of this disclosure.

In one embodiment as shown in FIG. 10, the PoC device 102 is similar to that shown in FIGS. 1A and 1B. However, the PoC device 102 in this embodiment does not comprise a screen. Instead, the PoC device 102 comprises a connection port 242 such as a Universal Serial Bus (USB) port (e.g., a micro-USB port or a USB Type C port) for physically and electrically coupling to a host computing-device such as a smartphone, a tablet, a laptop computer, a desktop computer, or the like. The host computing-device may execute a corresponding application program for controlling and collaborating with the PoC device 102 to perform tasks.

Figure 11:
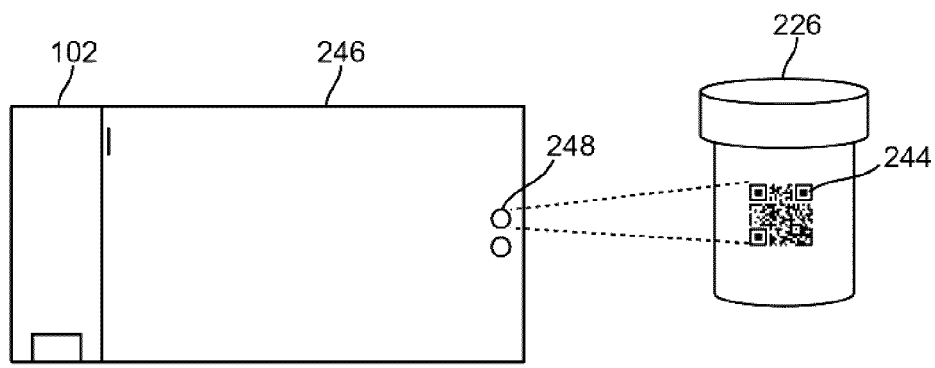
FIG. 11 shows the PoC device shown in FIG. 10 coupled to to a smartphone and uses the camera of the smartphone for reading the information of a two-dimensional barcode of a carrying vial to determine the type of biomarker of the electrochemical-sensor structures in the carrying vial, according to some embodiments of this disclosure.

For example, as shown in FIG. 11, the strip vial 226 comprises a QR-code 244 indicative of the type of the biomarker associated with the electrochemical-sensor structures 104 in the strip vial 226. The PoC device 102 is coupled to a smartphone 246 and uses the camera 248 of the smartphone 246 to read the QR code 244 on the strip vial 226 to determine the type of biomarker being that the electrochemical-sensor structures 104 can detect.

Figure 12:
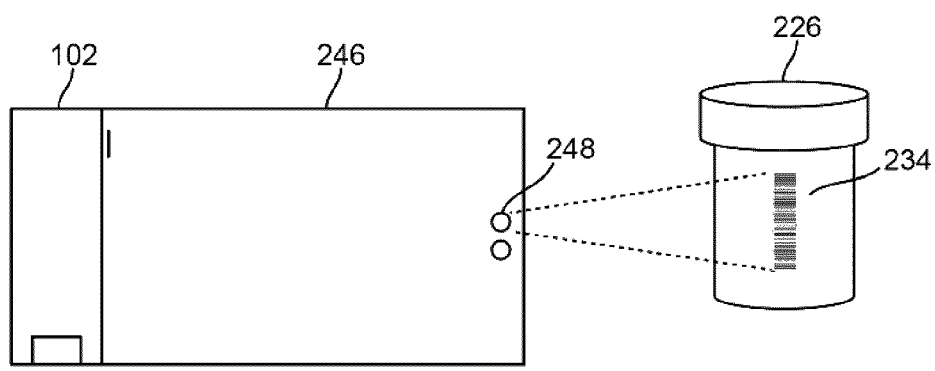
FIG. 12 shows the PoC device shown in FIG. 10 coupled to to a smartphone and uses the camera of the smartphone for reading the information of a one-dimensional barcode of a carrying vial to determine the type of biomarker of the electrochemical-sensor structures in the carrying vial, according to some embodiments of this disclosure.

In an embodiment as shown in FIG. 12, the strip vial 226 comprises a one-dimensional barcode 234 indicative of the type of the biomarker associated with the electrochemical-sensor structures 104 in the strip vial 226. The PoC device 102 is coupled to a smartphone 246 and uses the camera 248 of the smartphone 246 to read the one-dimensional barcode 234 on the strip vial 226 to determine the type of biomarker being that the electrochemical-sensor structures 104 can detect.

In some embodiments, the PoC device 102 may only comprise a potentiostat circuitry and/or detection circuitry and may be functionally coupled to a computing device such as a smartphone. In these embodiments, the PoC device 102 may leverage the smartphone's processor, screen, input (e.g., touchscreen, physical buttons, virtual buttons, and/or the like) and camera for the requisite computational power for displaying information to the user, and if needed, for scanning external inputs such as QR codes or one-dimensional barcodes.

Figure 13:
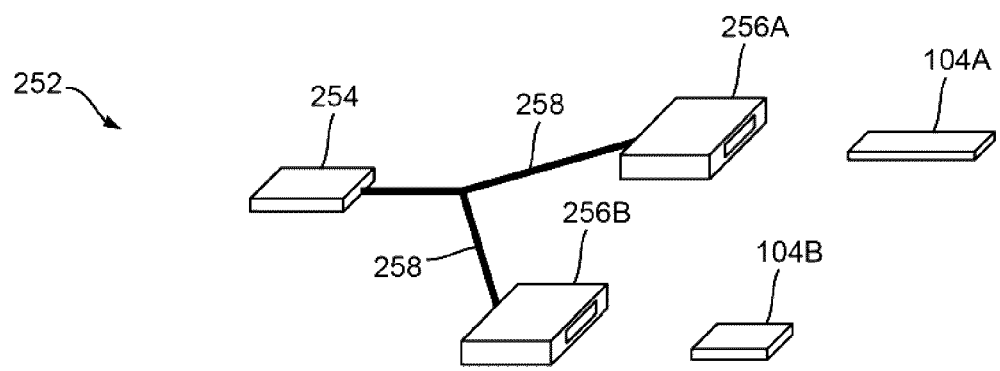
FIG. 13 shows a strip adapter for adapting to different types of electrochemical-sensor structures manufactured in accordance with different specifications, according to some embodiments of this disclosure.

In some embodiments, the portable electrochemical-sensor system 100 comprises a strip adapter 252 as shown in FIG. 13. The strip adapter 252 comprises a strip insert 254 with physical and electrical specifications suitable for inserting into the strip-receiving port 110 of the PoC device 102. The strip insert 254 is electrically connected to a plurality of strip receivers 256 such as the strip receivers 256A and 256B shown in FIG. 13, via electrical wiring 258. Each strip receiver 256A, 256B is configured for receiving a corresponding type of electrochemical-sensor structure 104A, 104B. In these embodiments, different types of electrochemical-sensor structures 104A and 104B may have different dimensions and may comprise different electrode configurations.

Figure 14:
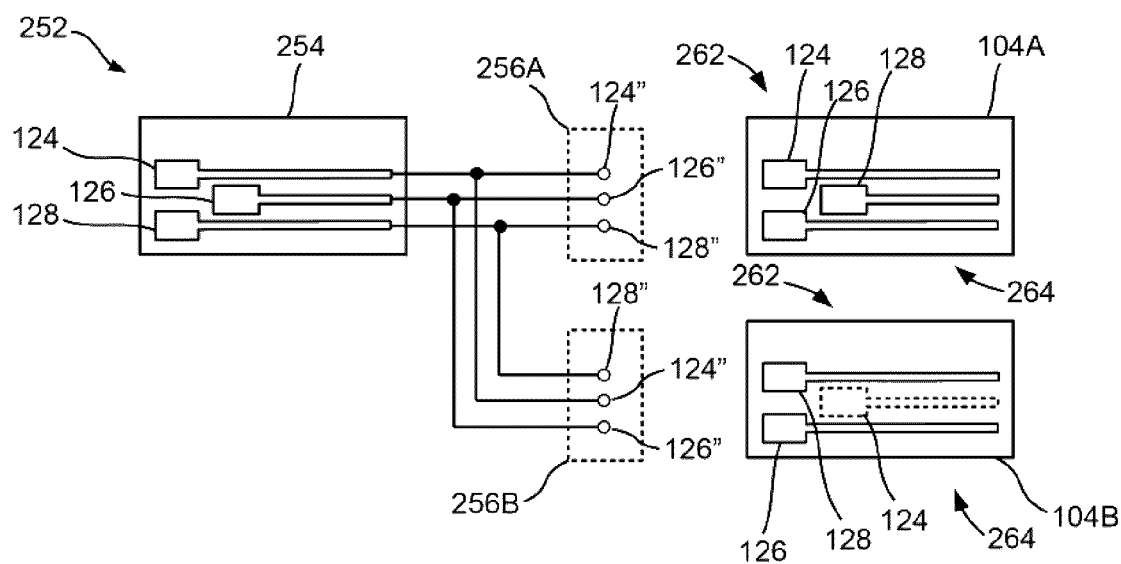
FIG. 14 is an electrical diagram of the strip adapter shown in FIG. 13.

For example, as shown in FIG. 14, the electrochemical-sensor structure 104A comprises, from a first lateral side 262 to a second lateral side 264 thereof, three electrodes RE 124, CE 126, and WE 128, all on a "top" side thereof. However, the electrochemical-sensor structure 104B comprises from a first lateral side 262 to a second lateral side 264 thereof, three electrodes WE 128, RE 124, and CE 126, wherein the electrodes WE 128 and CE 126 are on the "top" side thereof and the electrode RE 124 is on a "bottom" side thereof opposite to the "top" side (represented using broken lines).

Accordingly and as shown in FIG. 14, the strip receiver 256A has three electrical terminals 124", 126", and 128" arranged on a corresponding "top" side and in the same order as the electrodes 124, 126, and 128 of the electrochemical-sensor structure 104A for correctly engaging the electrodes WE 128, RE 124, and CE 126 thereof.

The strip receiver 256A has three electrical terminals 124", 126", and 128" arranged in the same order as the electrodes 124, 126, and 128 of the electrochemical-sensor structure 104B with the electrical terminals 126" and 128" on the corresponding "top" side and the electrical terminal 124" on a corresponding "bottom" side for correctly engaging the electrodes WE 128, RE 124, and CE 126 thereof.

Thus, the strip adapter 252 allows the PoC device 102 to adapt to different types of electrochemical-sensor structures 104 manufactured in accordance with different specifications such as electrochemical-sensor structures 104 made by different manufacturers.

In some embodiments, the strip adapter 252 does not comprise a strip insert 254. Rather, the strip adapter 252 comprises a wireless communication module for wirelessly coupling to the PoC device 102 for transferring testing data thereto.

Although in above embodiments, the PoC device 102 only comprises one strip-receiving port 110, in some alternative embodiments, the PoC device 102 may comprise a plurality of strip-receiving ports 110. The plurality of strip-receiving ports 110 may have the same physical and electrical specifications. Alternatively, at least some of the plurality of strip-receiving ports 110 may have different physical and electrical specifications for receiving different electrochemical-sensor structures 104 in a manner similar to that described above.

Although in above embodiments, the surface-area ratio of WE 128', CE 126', and RE 124' may be about 1:1:4, in some alternative embodiments, the surface-area ratio of WE 128', CE 126', and RE 124' may be determined based on the type of biomarker or antibody used on the electrochemical-sensor structure 104, or by the analyte that is targeted.

In some alternative embodiments, the surface-area ratio of WE 128', CE 126', and RE 124' may be determined based on the amount of detection element applied to the nanostructured-sensing surface of the electrochemical-sensor structure.

In some alternative embodiments, the ratio between the surface area of the electrodes WE 128', CE 126', and RE 124' and the surface area of the sample region 134 may be determined based on the electrochemical properties of the detection element or the biomarker that the electrochemical-sensor structure 104 is specific for.

In some embodiments, the ratio between the cross-sectional area of the sampling port 178 and the height thereof may be determined based on the electrochemical properties of the detection element or biomarker that the electrochemical-sensor structure 104 is specific for.

In some embodiments, the detection elements and geometric parameters for the electrochemical sensing structure are determined for detecting NT-pro-BNP.

In some embodiments, the nanostructured-sensing surface may be coated with a detection element having a high affinity and specificity for binding of the analyte.

In some embodiments, the nanostructured-sensing surface may be coated with a detection element having a high affinity and specificity for binding NT-pro-BNP.

In some embodiments, the electrochemical-sensor system 100 may be used for analyzing a sample fluid which may be any fluid having detectable biomarkers.

In some embodiments, one or more portable PoC devices 102 may be used in a health-monitoring computer-network system such as a computer-network system having an Artificial Intelligent (AI) based platform accessible through a software or firmware application running on a computer or a mobile device for assessing patient health data, filtering out frivolous health issues, providing accessible personalized health management advice to patients and communicating serious patient-specific health concerns to healthcare providers. The AI-based platform may utilize a neural network to process and analyze health data input from selected various sources and may produce a personalized assessment of an individual patient's health status. Such a health monitoring system may be used as a communication and monitoring tool by both physicians and patients and can streamline access to healthcare and reduce the strain on healthcare resources.

In some embodiments, the PoC device may comprise a communication module for connecting to an AI platform using suitable wired or wireless communication technologies such as Ethernet, WI-FI® (WI-FI is a registered trademark of Wi-Fi Alliance, Austin, TX, USA), BLUETOOTH® (BLUETOOTH is a registered trademark of Bluetooth Sig Inc., Kirkland, WA, USA), ZIGBEE® (ZIGBEE is a registered trademark of ZigBee Alliance Corp., San Ramon, CA, USA), 3G, 4G and/or 5G wireless mobile telecommunications technologies, and/or the like, for transmission of data collected from analyzing bodily fluid samples on the sample region of the electrochemical-sensor structure.

In some embodiments, the PoC device 102 may only transmit data to the AI platform when it obtains a valid reading of the data from the fluid sample applied to the sample region of the electrochemical-sensor structure.

In some embodiments, the PoC device 102 may further comprise other suitable peripheral components such as one or more positioning modules.

In some embodiments, the one or more positioning modules may be one or more global navigation satellite system (GNSS) components (e.g., one or more components for operation with the Global Positioning System (GPS) of USA, Global'naya Navigatsionnaya Sputnikovaya Sistema (GLONASS) of Russia, the Galileo positioning system of the European Union, and/or the Beidou system of China).

After the user's consent, the PoC device 102 may use the one or more positioning module to determine the geospatial information thereof such as the location, city, country, and the like, which may be used as the user's geospatial information. As those skilled in the art will appreciate, geospatial data provides situational context to a user's varying biomarker information thus providing a holistic assessment of the patient's health condition.

The obtained geospatial information may be sent from the PoC device 102 to a server via suitable communication technologies such as Wi-Fi, 3G, 4G, 5G cellular communication technologies, and the like.

The server may use the geospatial information collected from the PoC devices 102 for research in relevant fields such as prevalence and incidence of heart failures, understanding health resources utilization, frequent areas of re-hospitalizations, impact of low socioeconomic status on heart health, and the like, and for helping develop clinical pathways to assist healthcare systems and policy makers.

In some embodiments and upon the user's consent, geospatial or geo-fencing tracking may be implemented on the PoC device 102 (with collaboration of the server) to relegate patient history, current patient status, and current patient location to first responders.

In some embodiments, the PoC device 102 may collaborate with other health-monitoring devices and/or may have additional health-monitoring functionalities for providing a more comprehensive health-monitoring solution. For example, in some embodiments, the GNSS-integrated PoC device 102 may be used to track patients who have suffered or are at high risk of having a cardiac event. For a chronic condition like HF that requires constant if not intermittent biomarker level monitoring, "patient's door to treatment" time becomes very critical in cases of decompensation (from a steady state to am ore chronic health condition). This device will shorten the "event to treatment" time by providing the precise location of the patient, in urban, rural and remote settings.

In these embodiments, geospatial technology may be mission-critical to the PoC device 102. The primary value proposition that geomatics offers is emergency communication with geolocation in the event of a sudden cardiac event. For example, if a patient is responsive but cannot make a call, the patient can press a SOS button on the PoC device 102. An emergent communication such as an automated text report is then sent to one or more emergency services.

Those skilled in the art will appreciate that other embodiments are also readily available.

Figure 15A:
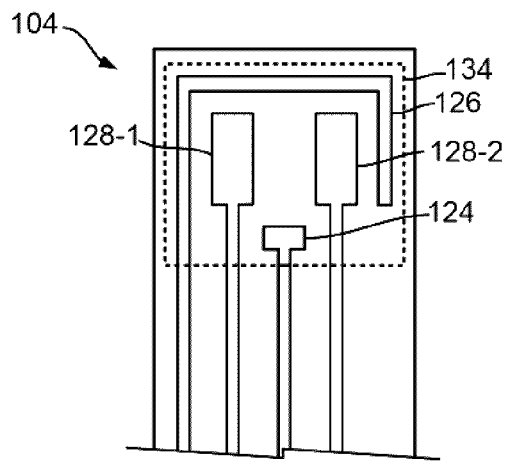
FIG. 15A is a schematic plan view of a portion of the electrochemical-sensor structure of the health monitoring system shown in FIG. 1A, according to some embodiments of this disclosure.

For example, FIG. 15A shows the electrochemical-sensor structure 104 according to some embodiments of this disclosure. In these embodiments, the electrochemical-sensor structure 104 is similar to that described above except that the electrochemical-sensor structure 104 in these embodiments comprises two WEs 128-1 and 128-2 with the RE 124 intermediate therebetween, and that the CE 126 extends about the WEs 128-1 and 128-2.

Figure 15B:
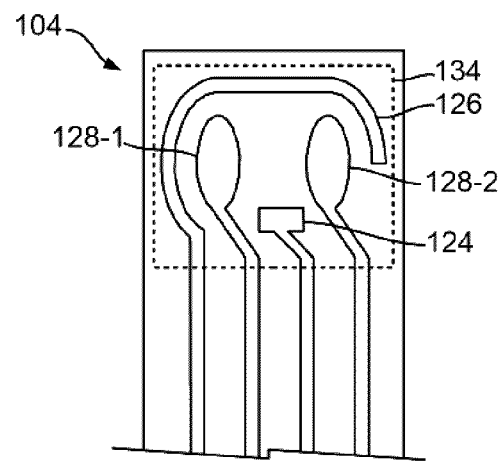
FIG. 15B is a schematic plan view of a portion of the electrochemical-sensor structure of the health monitoring system shown in FIG. 1A, according to yet some embodiments of this disclosure.

FIG. 15B shows the electrochemical-sensor structure 104 according to yet some embodiments of this disclosure. In these embodiments, the electrochemical-sensor structure 104 is similar to that shown in FIG. 15A except that the CE 126 in the sampling region 134 comprises a smoothly transiting trace and the two WEs 128-1 and 128-2 comprises oval-shape electrode terminals.

FIG. 15B shows the electrochemical-sensor structure 104 according to yet some embodiments of this disclosure. In these embodiments, the electrochemical-sensor structure 104 is similar to that shown in FIG. 15A except that the electrochemical-sensor structure 104 in these embodiments comprises an oval-shape CE 126 with a RE 124 and six (6) WEs 128 enclosed in the circle of the CE 126. The oval-shaped CE 126 is only electrically connected to the counter wiring CW 302 (indicated by a dot overlapping both) and the electrochemical-sensor structure 104 comprises a separation or isolating layer (not shown) sandwiched between the electrode components to electrically isolate the CE 126 from other electrodes (e.g., the RE 124 and the WEs 128).

Alternatively, the counter wiring CW 302 may be on a side of the substrate opposite to the side having the RE 124 and the WEs 128.

The electrodes of above-described electrochemical-sensor structure 104 may be fabricated via screen-printing or a sputter deposition process using conductive ink and conductive or semiconductive metals respectively.

Figure 17A:
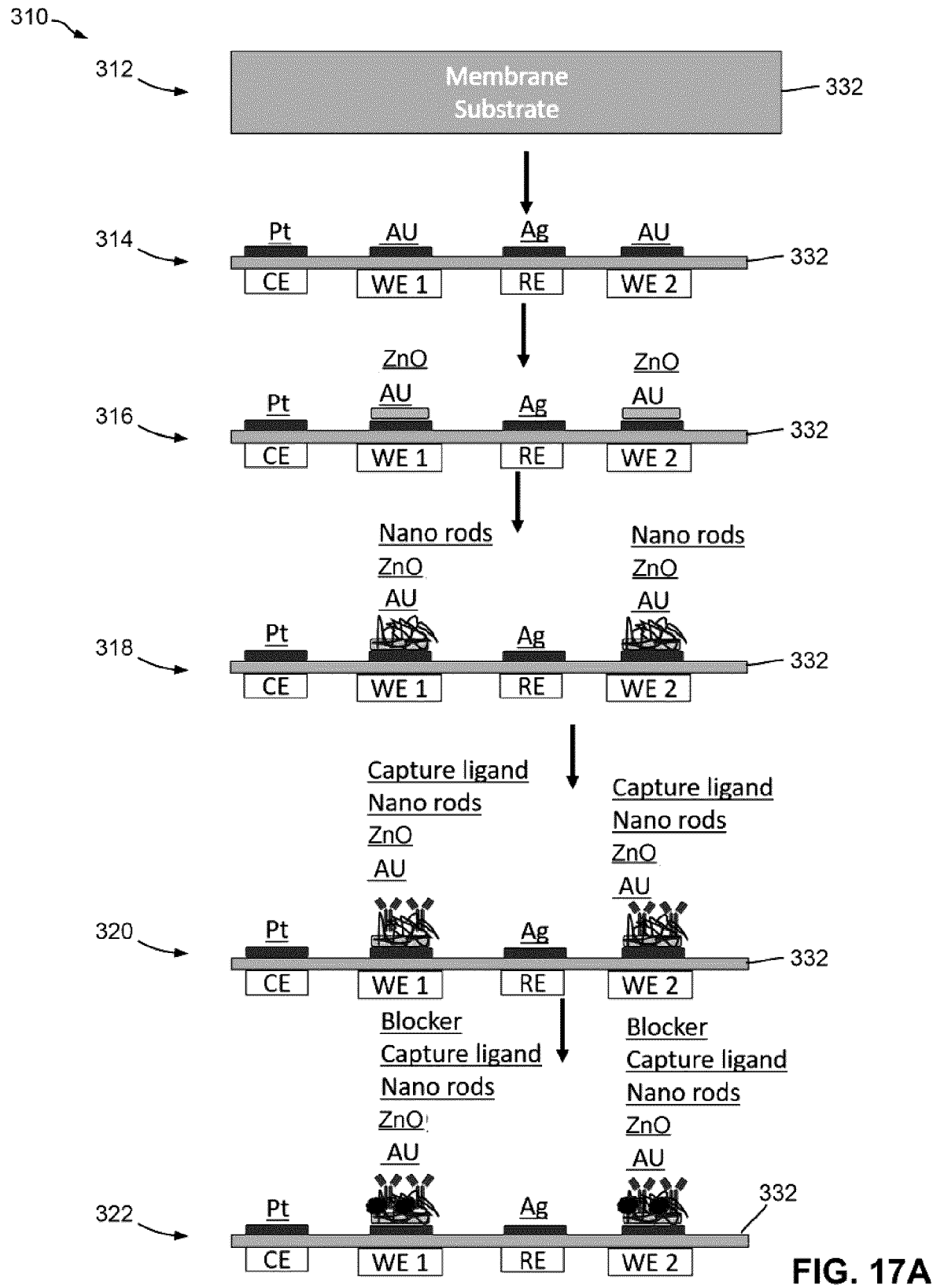
FIG. 17A shows the schematics of an exemplary fabrication process of screen-printed electrodes of the electrochemical-sensor structure of the health monitoring system shown in FIG. 1A, according to still some embodiments of this disclosure.
Figure 17B:
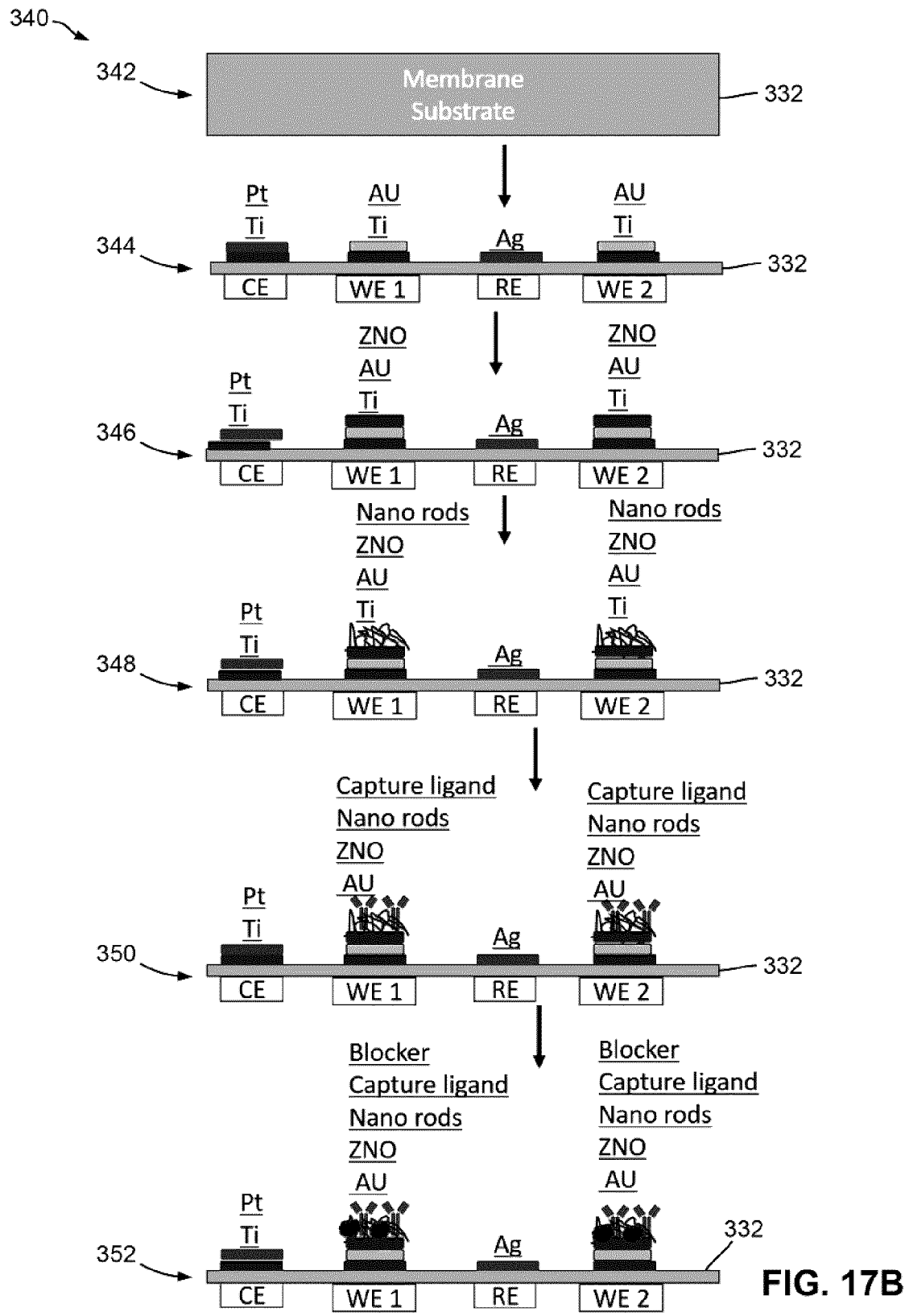
FIG. 17B shows the schematics of an exemplary fabrication process of sputtered electrodes of the electrochemical-sensor structure of the health monitoring system shown in FIG. 1A, according to still some embodiments of this disclosure.

FIG. 17A shows the schematics of an exemplary fabrication process 310 of screen-printed electrodes. FIG. 17B shows the schematics of an exemplary fabrication process 340 of sputtered electrodes. In these examples, three or more electrodes (denoted base electrodes) are fabricated onto a treated (i.e., modified) or untreated (i.e., unmodified) polymeric substrate 332 followed by screen printing.

As shown in FIGS. 17A and 17B, the substrate 332 is first prepared (FIG. 17A, step 312; FIG. 17B, step 342). Then, the base electrodes (e.g., CE, WE1, WE2, and RE) are manufactured using conductive or semiconductive material such as titanium, platinum, gold, chromium, silver, and/or the like, either as a single element or layer with other element with varying thickness (FIG. 17A, step 314; FIG. 17B, step 344).

The base electrode assembly may be sputter-coated with a metal oxide (e.g., ZnO) layer up to 100 nm (FIG. 17A, step 316; FIG. 17B, step 346). A highly organized metal-oxide nanostructures could be manufactured on top of seeded layer either electrochemically or hydrothermally (FIG. 17A, step 318; FIG. 17B, step 348). Then, a capture ligand may be crosslinked onto the surface of the newly synthesized nanostructures with an affinity for a specific analyte (FIG. 17A, step 320; FIG. 17B, step 350). To avoid non-specific binding of the interfering components, a generic blocker or a novel blocker could be integrated onto the sensing surface (FIG. 17A, step 322; FIG. 17B, step 352).

To characterize surface morphology and roughness of the fabricated electrodes and nanostructure components SEM, profilometry, TEM and AFM techniques may be used. Varied electrochemical techniques including but not limited to cyclic voltammetry, amperometry and EIS may be utilized to obtain electrochemical data and set standards. Moreover, Fourier transform infrared spectroscopy (FTIR) and X-ray diffraction (XRD) may be used to analyses the elemental composition of the said assembly.

Figures 18A, 18B, 18C, 18D, 18E:
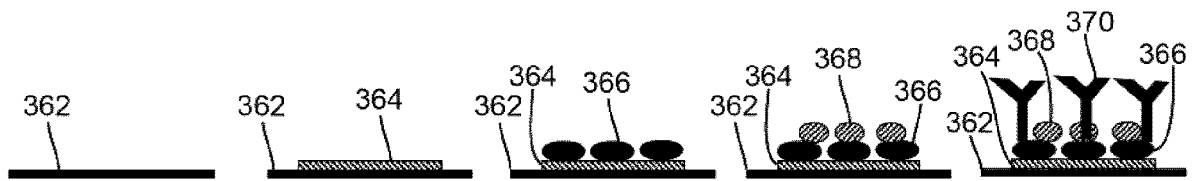
FIGS. 18A to 18E illustrates the progression of a deposition process for fabricating an electrode of the electrochemical-sensor structure of the health monitoring system shown in FIG. 1A, according to still some embodiments of this disclosure.

FIGS. 18A to 18F illustrates the progression of a deposition process, wherein FIG. 18A shows a test strip with bare electrode 362, FIG. 18B shows nanorod deposition 364 on the electrode 362, FIG. 18C shows crosslinkers 366 deposited on the nanorod deposition 364, FIG. 18D illustrates a blocking agent 368 deposited on the crosslinker 366, and FIG. 18E illustrates antibodies 370 deposited on the electrode 362.

Figure 18F:
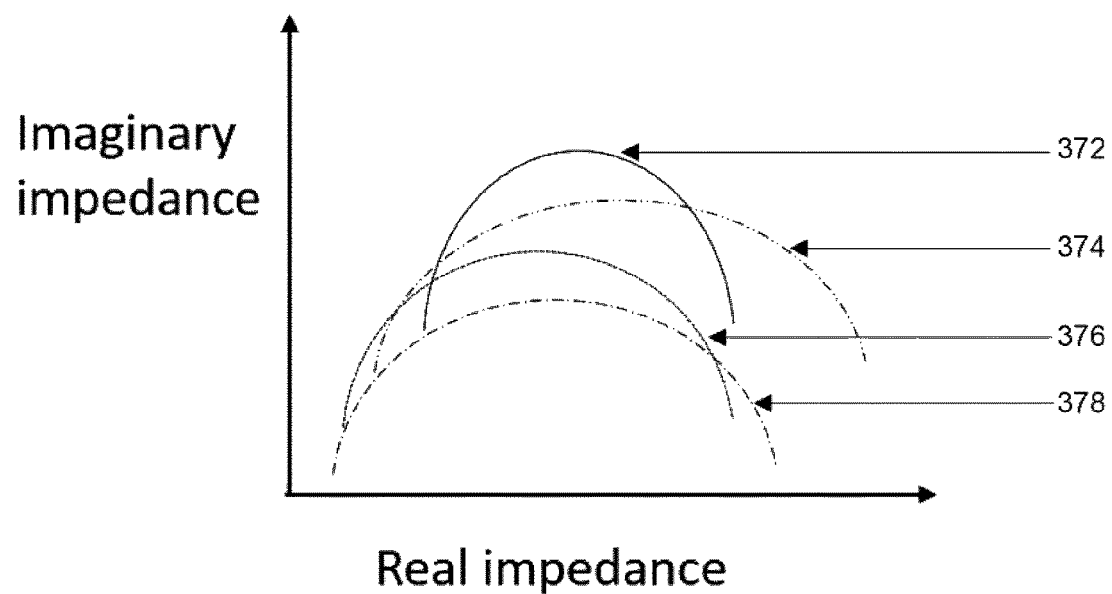
FIG. 18F is a graph showing the measurement of the quality of strip including the quality of deposited or immobilized biosensors, organic chemicals, bio-linkers and nanorods.

FIG. 18F is a graph showing the measurement of the quality of the electrode-bearing test strip including the quality of deposited or immobilized biosensors, organic chemicals, bio-linkers and nanorods, wherein the horizontal axis represents Real-impedance measurements, and the vertical axis represents the Imaginary-impedance measurements. Each of the curves 372 to 378 is obtained from an EIS measurement of the strip 104 under different surface conditions. The curve 372 represents an ideal immobilization condition shown in FIG. 18E which contains antibodies 370, a blocking agent 368, a crosslinking agent 366 and a nanorod layer 364 immobilized on the electrode 362.

Figure 19:
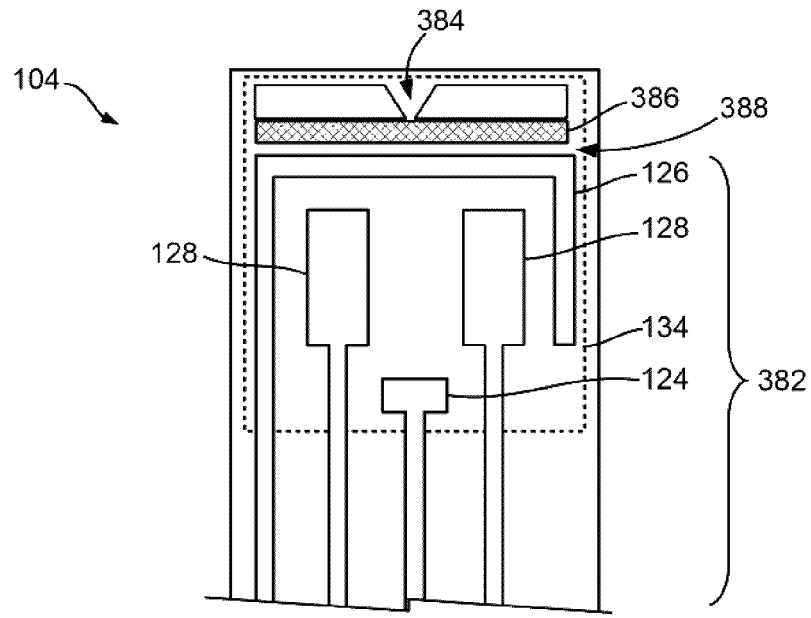
FIG. 19 is a top view of the electrochemical-sensor structure of the health monitoring system shown in FIG. 1A, according to still some embodiments of this disclosure, the electrochemical-sensor structure comprising an introductory channel followed by a heterophile plasma separating component (HF-PSC) unit adjacent the electrodes.

FIG. 19 is a schematic plan view of an electrochemical-sensor structure 104 having an assembly 382 of multiple electrodes (e.g., a CE, a RE, and two to six WEs), according to some embodiments of this disclosure. The electrochemical-sensor structure 104 comprises one or more introductory channels 384 for introducing the fluid sample using the capillary effects to a heterophile plasma separating component (HF-PSC) unit 386 adjacent thereto. The HF-PSC unit 386 is in proximity with and spaced from the electrode assembly 382 with a gap therebetween forming an analyte-drop chamber 388.

The one or more introductory channels 384 may be engraved on the substrate 112, or alternatively may be formed by a suitable material coated onto the substrate 112 with gaps therein forming the introductory channels 384. The one or more introductory channels 384 may have any suitable geometric shape or dimension. In the example shown in FIG. 19, the electrochemical-sensor structure 104 comprises one funnel-shape introductory channel 384 having an opening adjacent the edge of the sampling region 134 and tapering towards the HF-PSC unit 386.

Figure 20:
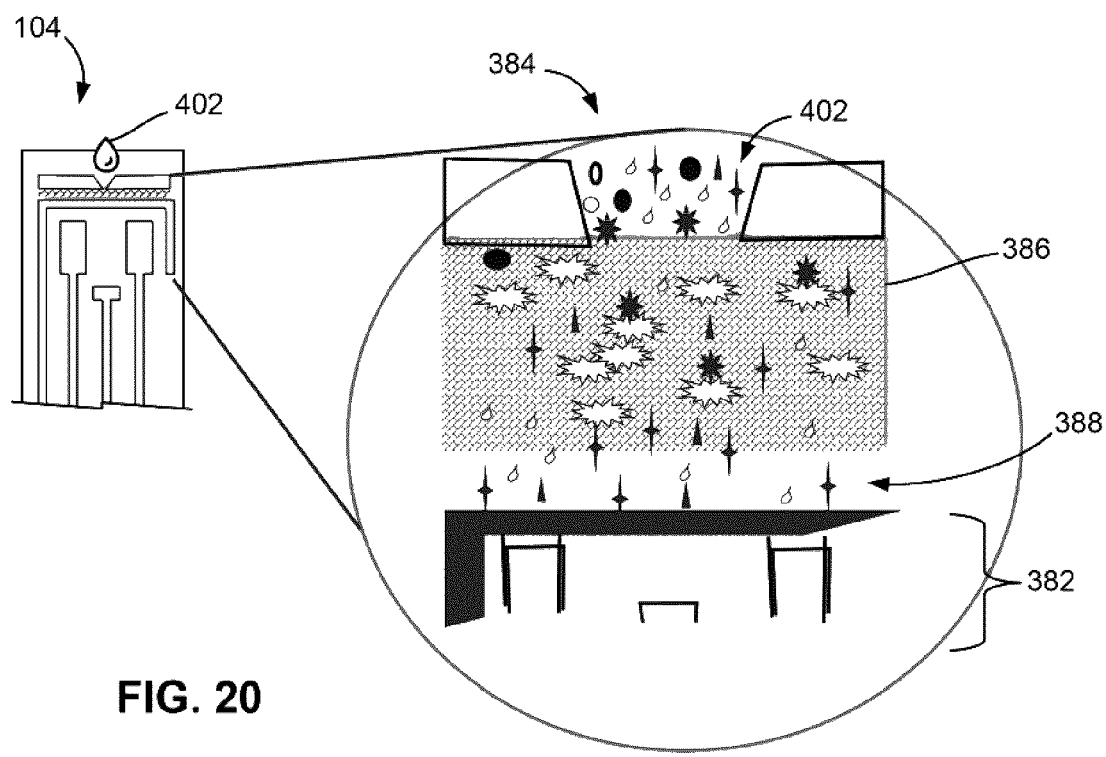
FIG. 20 is schematic diagram of the electrochemical-sensor structure shown in FIG. 19 showing a fluid sample passing through the introductory channel and the HF-PSC unit into an analyte-drop chamber for contacting the electrodes.

As shown in FIG. 20, when a bodily fluid 402 is dropped to the introductory channel 384 which utilizes surface-tension properties of the dropped bodily fluid 402 for efficient flow dynamics and therefore reducing volume requirement for the quantification assay.

The introductory channel 384 funnels the dropped bodily fluid 402, wherein the analyte along with other fluid components travels through the HF-PSC unit 386. The HF-PSC unit 386 is a separator component embedded with specific blocker component to filter out unwanted interfering components of the fluid 402 and capture or retain therein interfering fluid components that may otherwise elicit false positive or false negative results in the assay. The HF-PSC unit 386 may be modified and/or treated to capture interfering fluids components for increased sensitivity and selection. In various embodiments, the HF-PSC unit 386 may comprise symmetrical and/or asymmetrical pores with varied pore sizes. In some embodiments, the HF-PSC unit 386 may alternatively be untreated depending on the application of the assay.

The filtered fluid sample obtained in the HF-PSC unit 386 then enters the analyte-drop chamber 388 for contacting the electrode assembly 382 which comprises the base electrodes with or without layered nanostructures and cross-linked capture ligand for a specific analyte (WE, CE and RE respectively). In various embodiments, the number of WE electrodes may vary depending on the assay type and multiplexing of the assay.

Figure 21:
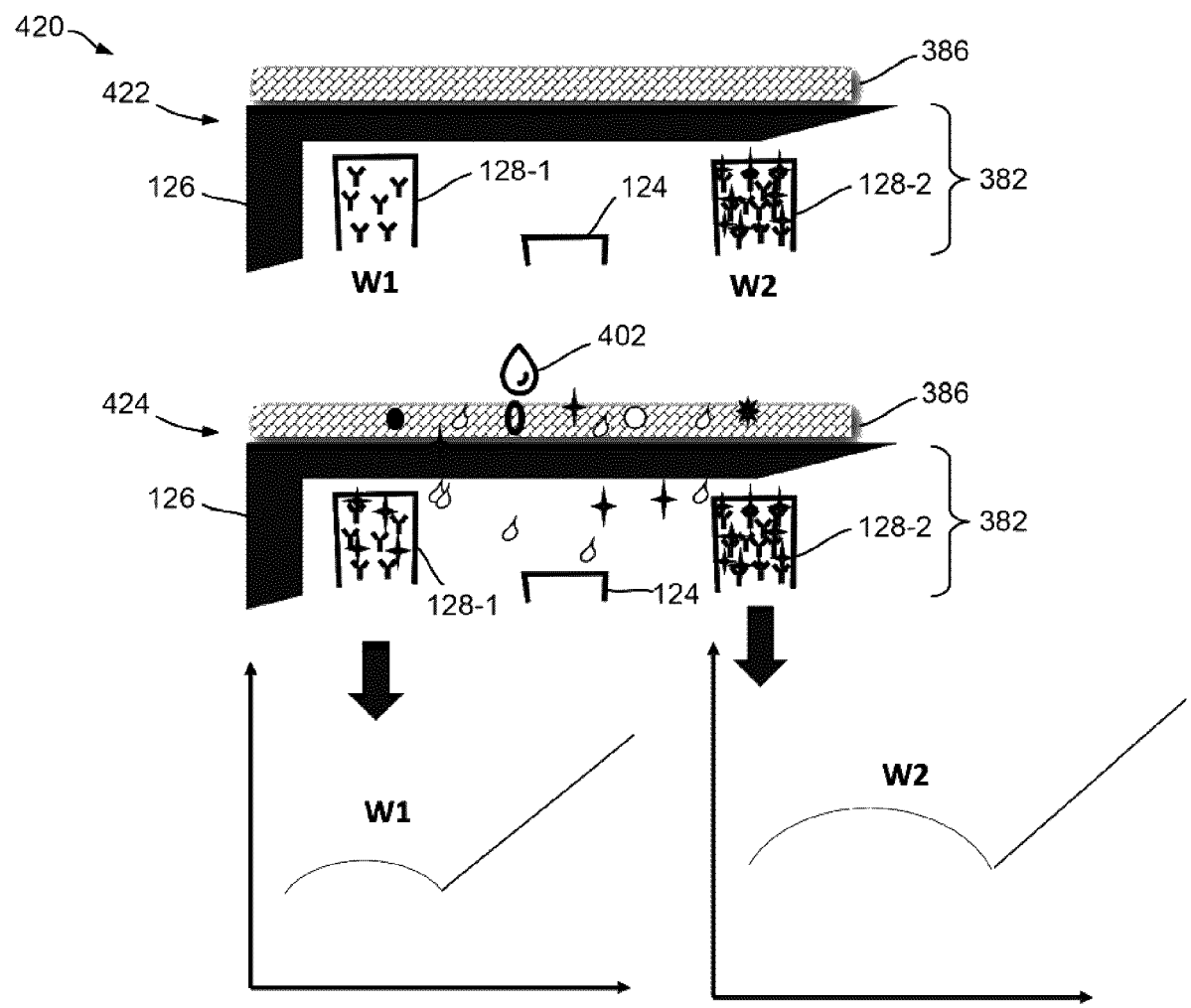
FIG. 21 shows a working schema for the quantification of analyte from body fluids for an electrode assembly of two to six working-electrode system.

FIG. 21 shows a working schema 420 for the quantification of analyte from body fluids for an electrode assembly of two to six working-electrode system, showing one of the working electrodes embedded and oversaturated with the desired capture ligand, interaction of body fluid components with embedded oversaturated ligand, and a simplified conceptual EIS graph indicating analyte quantification.

As shown, one of the WEs 128 such as the WE 128-2 is oversaturated with capture ligand while the other WE 128-1 is cross-linked with predefined concentration of similar or different capture ligand (step 422). The quantification values are derived from previously run experiments defining standard curves for both desired and interfering entities. The PoC device 102 then uses a mathematical model for calculating the final output value in terms of EIS values (obtained in steps 422 and 424) to determine real assay value of the said analyte as:

$$\text{Analyte concentration} = \text{Rct}_{WE2} - \text{Rct}_{WE1},$$

where $\text{Rct}_{WE1}$ and $\text{Rct}_{WE2}$ are the resistances to charged electron transfer (RCT, also denoted as "charge transfer resistance") of electrodes WE1 and WE2, respectively.

In the embodiments shown in FIGS. 19 to 21, the electrochemical-sensor structure 104 comprises two WEs 128 with one WE oversaturated with capture ligand (denoted as oversaturated WE) and the other WE cross-linked with predefined concentration of similar or different capture ligand (denoted experimental WE). The analyte concentration is calculated based on the difference of the RCTs of the oversaturated WE and the experimental WE.

Figure 16:
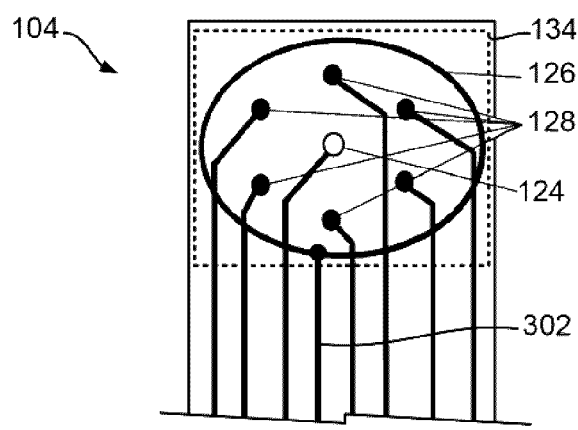
FIG. 16 is a schematic plan view of a portion of the electrochemical-sensor structure of the health monitoring system shown in FIG. 1A, according to still some embodiments of this disclosure.

In some embodiments wherein the electrochemical-sensor structure 104 comprises more than two WEs 128 (e.g., as shown in FIG. 16), one or more WEs may be configured to be oversaturated WEs and other WEs may be configured to be experimental WEs. The analyte concentration is calculated based on the differences of the RCTs of the oversaturated WEs and the experimental WEs by using a suitable statistical method such as a maximum likelihood estimator, a least-square estimator, minimum mean square error (MMSE) estimator, and/or the like.

Figure 22:
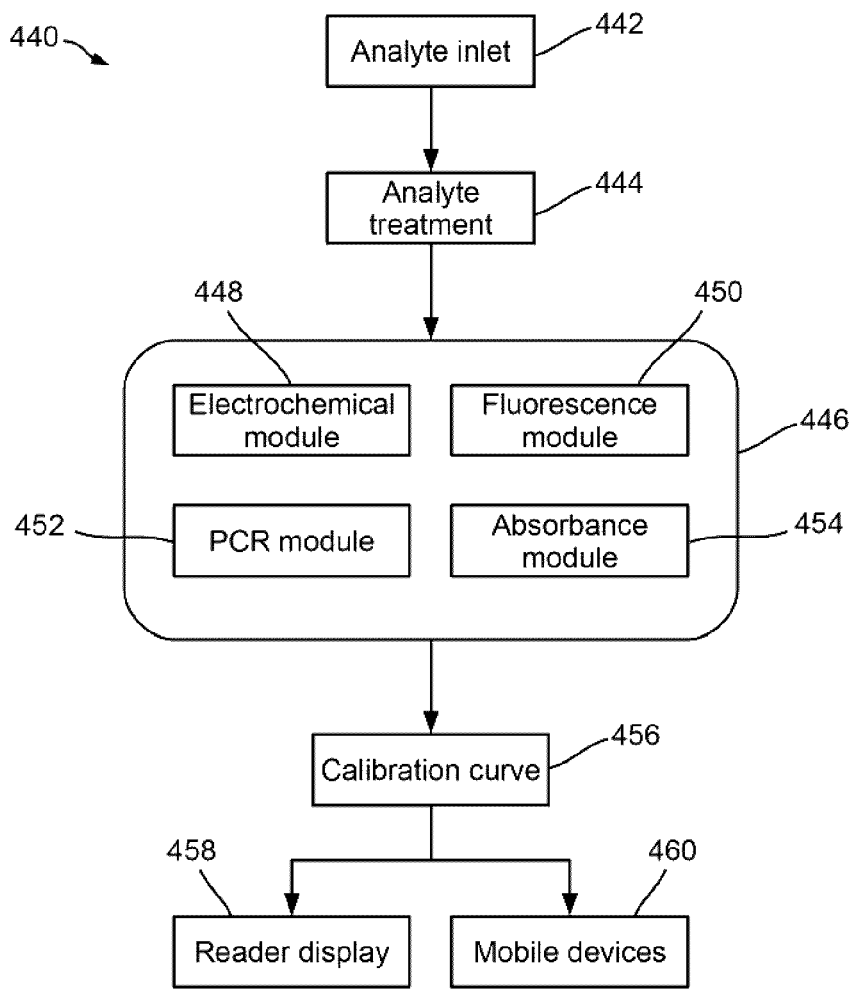
FIG. 22 is a block diagram showing a modular structure of the PoC device of the health monitoring system shown in FIG. 1A for bodily fluid analysis.

FIG. 22 is a block diagram showing a modular structure 440 of the electrochemical-sensor system 100 for bodily fluid analysis. As shown, the analyte enters the electrochemical-sensor structure 104 via an analyte inlet 442 (e.g., a capillary inflow for blood sample as described above) and is treated by an analyte treatment module 444 thereof which may be imparted through a substrate resulting in mixing the blood with a complex. Such a treatment results in an eventual plasma separation that contains a complex enabling efficient downstream processing.

The output of the analyte treatment module 444 is sent to a multi-module setup 446 of the PoC device 102 comprising an electrochemical module 448, a fluorescence module 450, a polymerase chain reaction (PCR) module 452, and an absorbance module 454, which, in some embodiments, may be combined or otherwise integrated into a single miniaturized module. Herein, the multi-module setup 446 allows the user to switch to a suitable one of the modules 448 to 454 for blood analysis. For example, the NT-pro-BNP detection requires the electrochemical module 448, the fluorescence module 450 and the PCR module 452 may operate together to enable aptamer-based ligand recognition, and metabolite panel may require the absorbance module 454.

The calibration curve module 456 may be a memory of the PoC device 102 or a memory on a secure central-server, storing a calibration curve (i.e., a calibrated dataset). In some embodiments, the PoC device 102 may communicate with a central server to obtain a calibration curve associated with the lot/batch of the strip 104.

In some embodiments, screen-printing technology may be used to create an arrangement of electrodes resulting in impedance-coded recognition of lots/batch of strips. Using this code, the PoC device 102 may communicate with the central server to establish accurate calibration curve prior to analyte analysis.

Raw data from the multi-module setup 446 is transmitted securely to the memory 456 and compared with the calibration curve stored therein to obtain biologically relevant measurands (e.g., biomarker concentration obtained through EIS) in appropriate units. The obtained measurands are then displayed in the display 458 of the PoC device 102, and/or transmitted to related mobile devices 460 (e.g., the user's mobile device and/or the doctor's mobile device) via suitable wired or wireless communication technologies such as BLUETOOTH®, and displayed thereon.

In some embodiments, the values obtained through EIS may also be used for diagnosing the efficacy of the immobilized biosensors. For example, in one embodiment, an EIS sweep may be performed to estimate the "health" of the substrate before applying fluid sample thereto.

Figure 23:
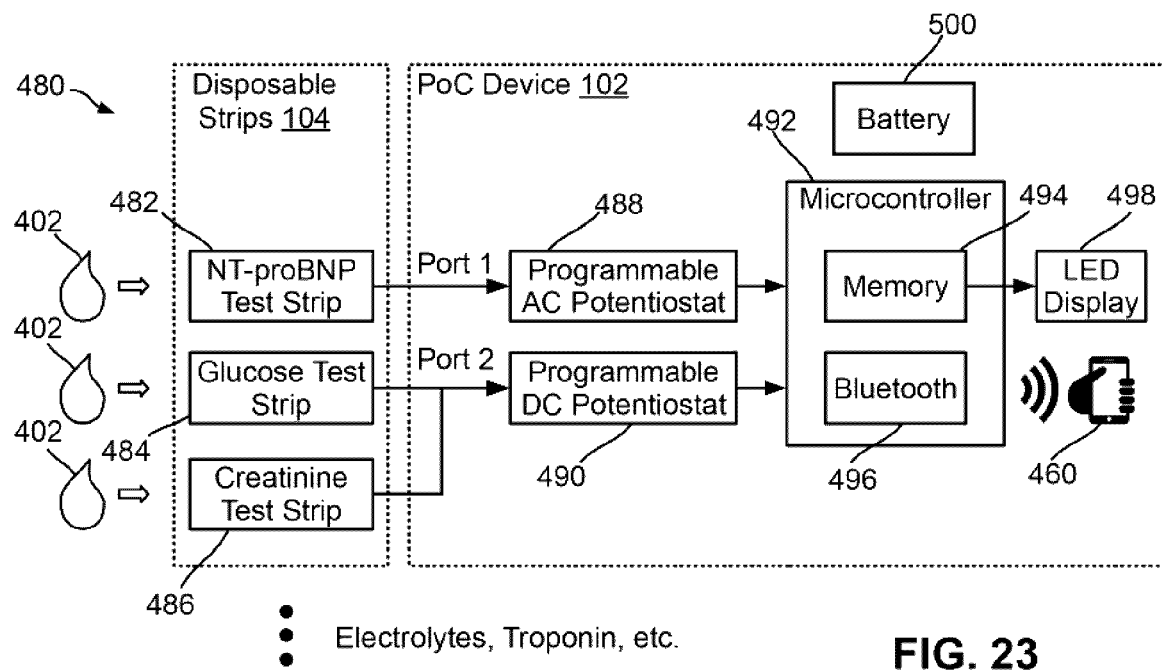
FIG. 23 is a block diagram showing a modular structure of the PoC device of the health monitoring system shown in FIG. 1A for bodily fluid analysis, according to some embodiments of this disclosure.

FIG. 23 is a block diagram showing a modular structure 480 of the PoC device 102 for blood analysis, according to some embodiments of this disclosure. As shown, the PoC device 102 may be used with a plurality of electrochemical-sensor structure or disposable strips 104 for blood analysis, such as a NT-pro-BNP test strip 482 for detecting NT-pro-BNP biomarker in human blood samples, a glucose test strip 484, a creatinine test strip 486, and other suitable strips (e.g., strips for testing electrolytes, troponin, and/or the like). The strips 104 (e.g., the strips 482 to 486) have a universal strip adaptor to interface with the PoC device 102.

The PoC device 102 comprises a programmable AC potentiostat circuitry 488 and a programmable DC potentiostat circuitry 490 which, including voltage control and data storage and analysis, are controlled by a control circuitry 492 (e.g., an Arduino microcontroller) having necessary components such as a memory 494 and a communication module 496 (e.g., a Bluetooth module). The PoC device 102 also comprises a light-emitting diode (LED) display 498 (or other suitable display) and a battery 500 for power various components.

Based on the type of test, the PoC device 102 may automatically use the programmable AC potentiostat circuitry 488 or the programmable DC potentiostat circuitry 490 for testing. The testing results are transmitted to the control circuitry 492 for analysis and stored in the memory 494 thereof. The analytical result is displayed on the LED display 498 and/or securely and wirelessly transmitted to a mobile device 460 and displayed thereon.

In some embodiments, fluid-flow channels may work in congruence with the electrode system. Prior-art systems have used multiple electrodes to assess the quantity of fluid present inside the flow channel. In efforts to miniaturize the strip design, a combination of channel geometry and electrode design is used. As will be described in more detail later, in some embodiments, a channel or microchannel may be accessed through an inlet port. On the opposite side of the inlet port, there may be constriction across the channel's cross-section. In related embodiments, the substrate may be treated to be hydrophobic which prevents fluid flow. By measuring the change in current from the electrode, the stability of the fluid flow may be assessed.

In some embodiments, the dimension of the microchannel is predetermined to obtain a predetermined volume so as to allow complete filling of fluid.

Figure 24A:
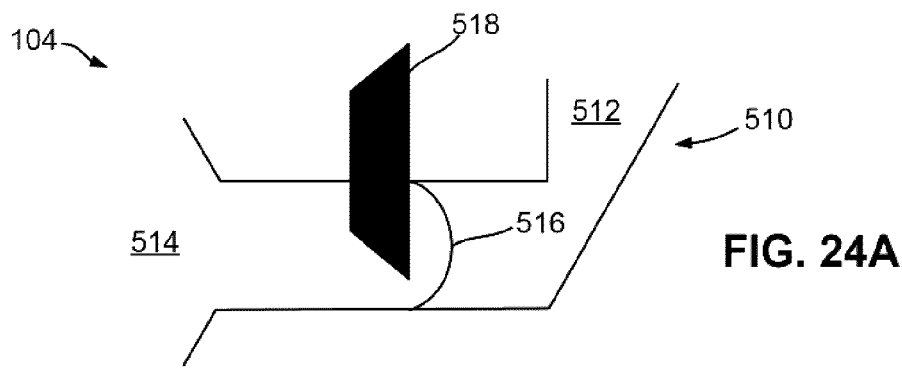
FIGS. 24A and 24B show a hybrid design of the electrochemical-sensor structure of the health monitoring system shown in FIG. 1A with control of the flow stability and the volume of the fluid sample received in the sampling region thereof, according to some embodiments of this disclosure.
Figure 24B:
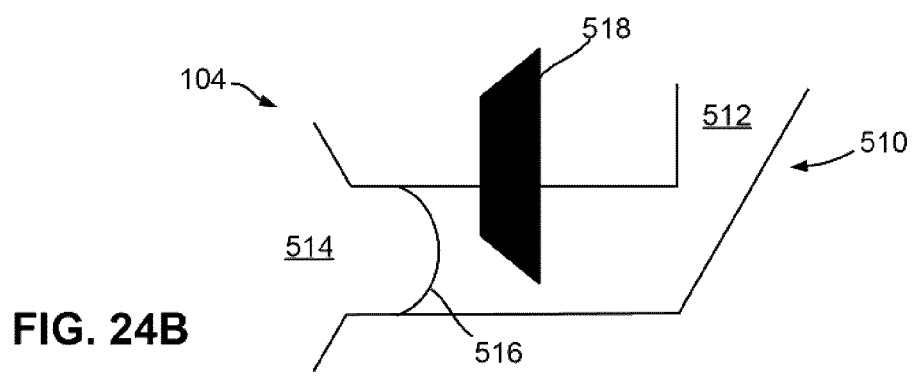

FIGS. 24A and 24B show a hybrid design of the electrochemical-sensor structure 104 with control of the flow stability and the volume of the fluid sample received in the sampling region thereof, according to some embodiments of this disclosure.

As shown in FIG. 24A, the electrochemical-sensor structure 104 comprises one or more capillary channels 510 (also denoted microchannels or microfluidic channels) with an entrance or inlet opening 512 in or about the analyte-drop chamber 388 and extending from the analyte-drop chamber 388 to the electrode area.

The one or more capillary channels 510 may be engraved or otherwise formed on the substrate 122 and may be hydrophilic to the fluid sample. Each microchannel 510 comprises a substantially abrupt expansion 514 (i.e., a substantially abrupt increase of the width and/or the cross-sectional area thereof) with the distance between the entrance 512 and the expansion 514 predetermined based on the fluid-volume requirement.

An electrode 518 such as a WE extends to the microchannel 510 at a location intermediate the entrance 512 and the expansion 514 (i.e., the electrode 518 is downstream to the entrance 512 and upstream to the expansion 514) and is capable to directly interact with the fluid sample therein. Thus, the electrode 518 may be used for inspecting the sample through a DC potentiostat circuitry, an AC potentiostat circuitry, or a combination thereof.

During the sampling of a bodily fluid, the fluid flow enters the microchannel 510 from the entrance 512 and flows therein. FIG. 24A shows the flow front 516 approaching the electrode 518. FIG. 24B shows the flow front 516 passing the electrode 518.

The abrupt expansion 514 and the surface tension effects associated therewith impede the flow front of the fluid flow in the microchannel 510 and thus controls the fluid volume. When the flow front 516 has not approached the electrode 518, the impedance scanned by the electrode 518 is low. When the flow front 516 passes the electrode 518, the impedance scanned by the electrode 518 may steadily increase thereby indicating the passage of the flow front 516.

In some embodiments, the abrupt expansion 514 and the surface tension effects associated therewith may also be employed for controlling the fluid velocity.

The electrode 518 may be electrically coupled to the DC potentiostat circuitry 490 (see FIG. 23) which applies a DC voltage to the electrode 518 and monitors the rate of current change. If the rate of current becomes zero with a high impedance measurement (e.g., greater than a predefined impedance threshold), it means that the microchannel 510 receives therein blood but with no flow. If the rate of current is non-zero with a high impedance measurement (e.g., greater than the predefined impedance threshold) for more than a predetermined period of time, it means that the amount of blood in the microchannel 510 is satisfactorily acceptable for the strip test.

Figure 25A:
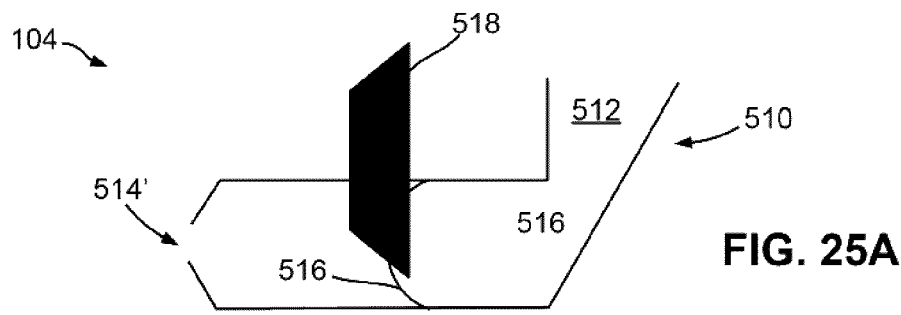
FIGS. 25A to 25C show the electrochemical-sensor structure of the health monitoring system shown in FIG. 1A with control of the stability and volume of the fluid sample flow received in the sampling region thereof, according to yet some embodiments of this disclosure.
Figure 25B:
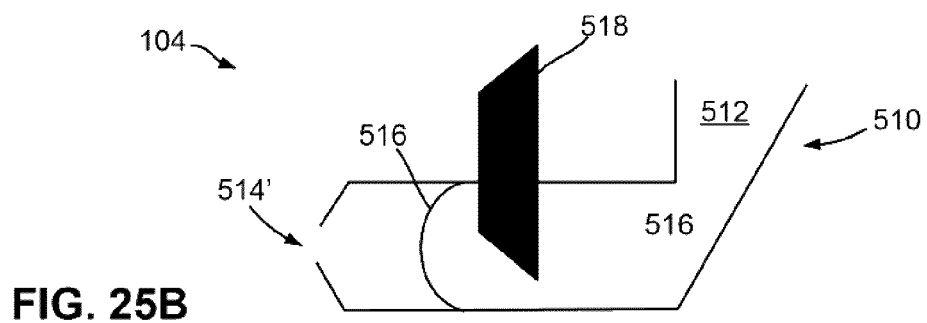
Figure 25C:
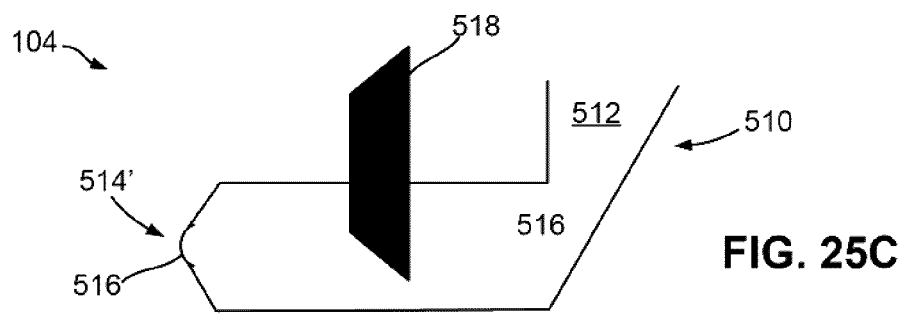

FIGS. 25A to 25C show the electrochemical-sensor structure 104 with control of flow stability and volume of the fluid sample received in the sampling region thereof, according to yet some embodiments of this disclosure.

The electrochemical-sensor structure 104 in these embodiments is similar to that shown in FIGS. 24A and 24B and comprises one or more microchannels 510 with an entrance or inlet opening 512 in or about the analyte-drop chamber 388 and extending from the analyte-drop chamber 388 to the electrode area. The one or more capillary channels 510 may be engraved or otherwise formed on the substrate 122 and may be hydrophobic to the fluid sample.

As shown, each microchannel 510 comprises a substantially abrupt tapering portion 514' (i.e., a substantially abrupt decrease of the width and/or the cross-sectional area thereof) for controlling the fluid volume. The distance between the entrance 512 and the tapering portion 514' is predetermined based on the fluid-volume requirement.

An electrode 518 such as a WE extends to the microchannel 510 at a location intermediate the entrance 512 and the tapering portion 514' (i.e., the electrode 518 is downstream to the entrance 512 and upstream to the tapering portion 514') and is capable to directly interact with the fluid sample therein. The electrode 518 may be used for inspecting the sample through a DC potentiostat circuitry, an AC potentiostat circuitry, or a combination thereof.

Figure 26:
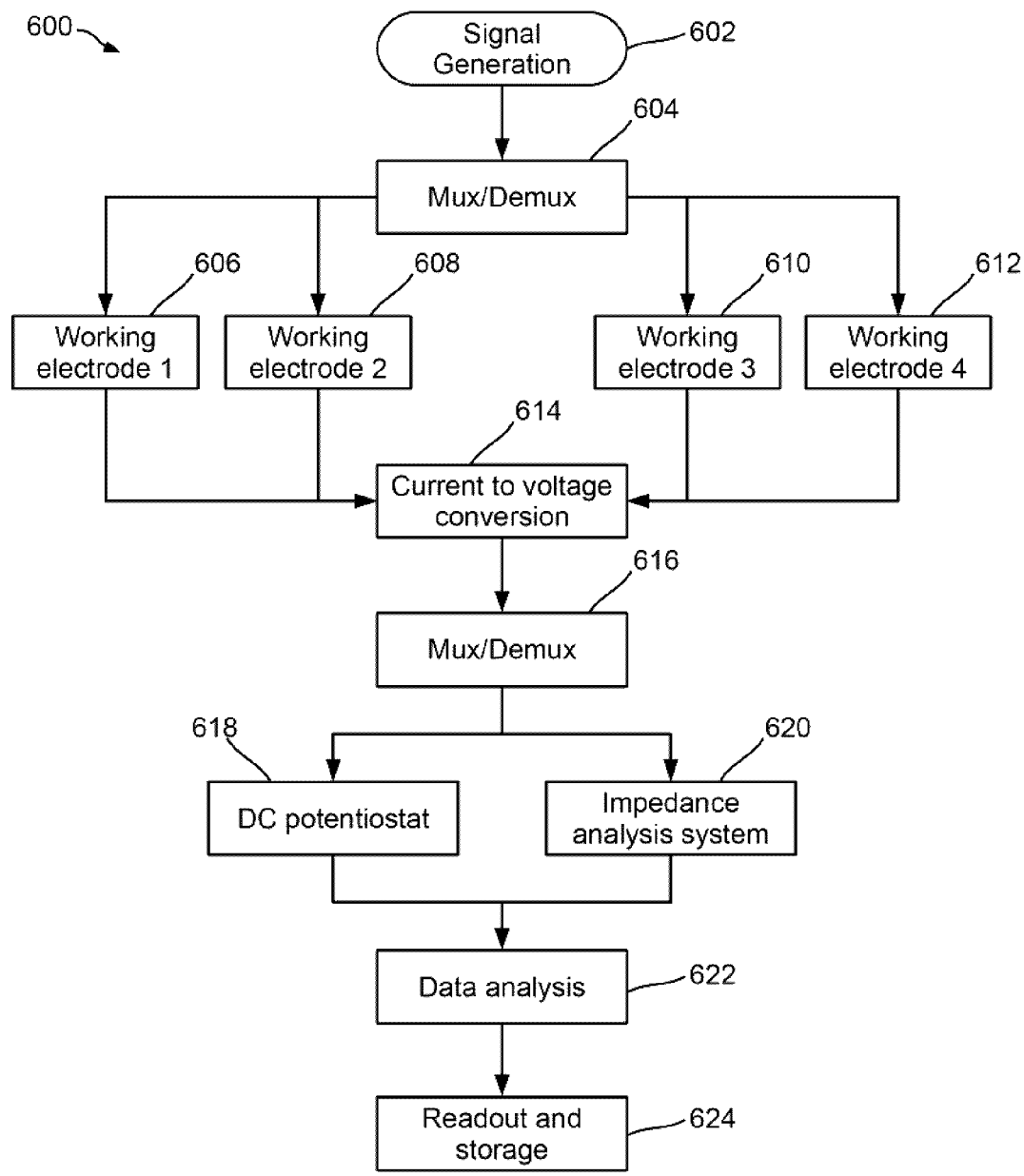
FIG. 26 is a flowchart showing a process executed by the PoC device of the health monitoring system shown in FIG. 1A for bodily fluid analysis, according to some embodiments of this disclosure.

FIG. 26 is a flowchart showing a process 600 executed by the PoC device 102 for bodily fluid analysis, according to some embodiments of this disclosure. As shown, a signal generator 602 of the PoC device 102 outputs a signal (e.g., an AC signal) to the WEs 606 to 612 via a multiplexer/demultiplexer (mux/demux) 604. The signals from the WEs 606 to 612 are fed to a multi-channel current-to-voltage converter 614 for outputting voltage signals to either a DC potentiostat circuitry 618 or an AC potentiostat circuitry 620 via the mux/demux 616. The outputs of the DC potentiostat circuitry 618 and/or AC potentiostat circuitry 620 are analyzed by a data analysis module 622. The analytical results of the data analysis module 622 are readout, displayed and/or stored at the output module 624.

Figure 27:
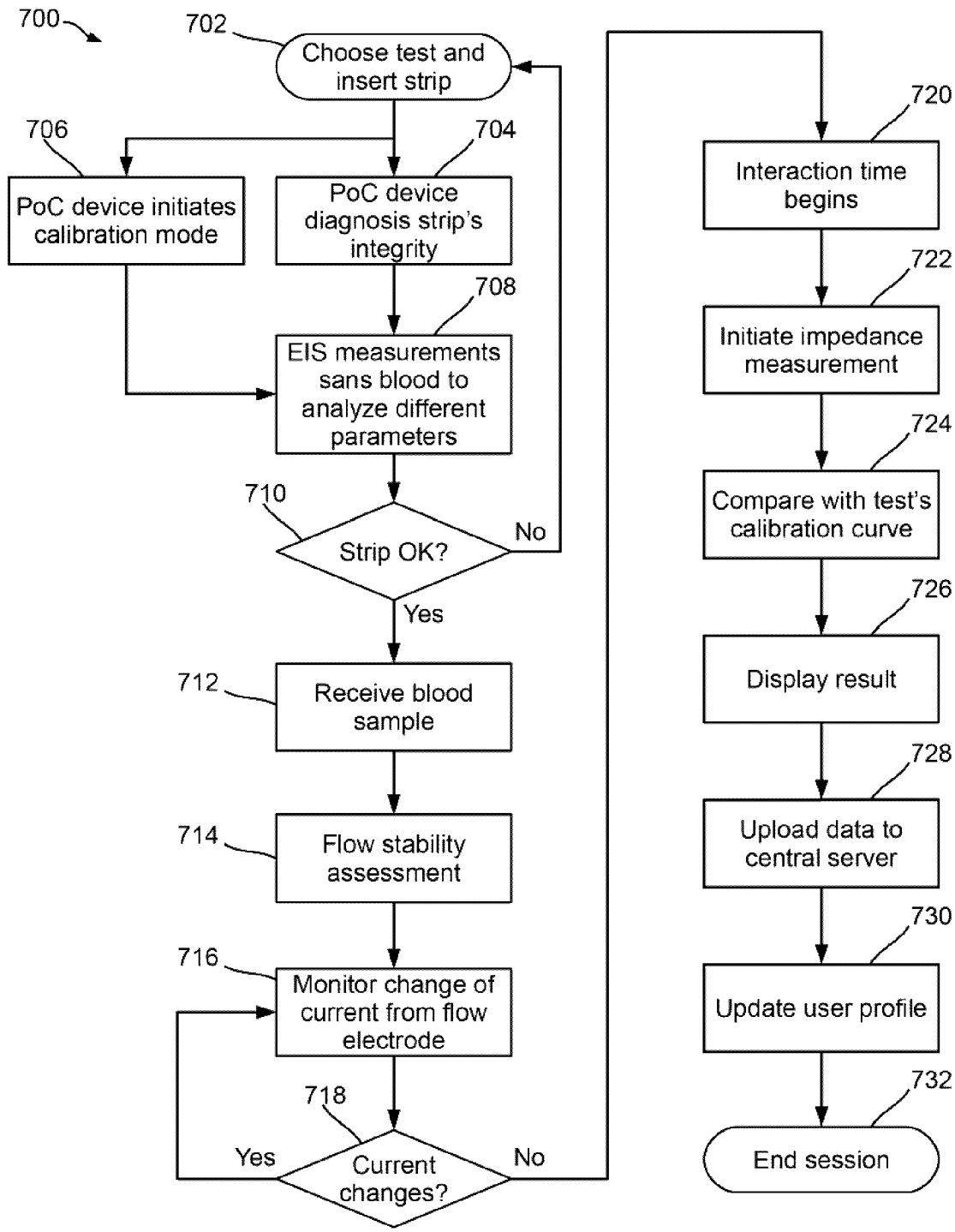
FIG. 27 is a flowchart showing a process executed by the PoC device of the health monitoring system shown in FIG. 1A for bodily fluid analysis, according to yet some embodiments of this disclosure.

FIG. 27 is a flowchart showing a process 700 executed by the PoC device 102 for bodily fluid analysis, according to some embodiments of this disclosure. The process 700 starts when a user chooses the type of test and the strip 104 to use (step 702). When the strip 104 is inserted into the PoC device 102, the PoC device 102 diagnoses the strip 104 for quality of substrate and integrity of biosensor components (step 704). If the test is impedance-based, the PoC device 102 automatically calibrates itself to an impedance range suitable for the biomarker under inspection (step 706). The PoC device 102 also checks the type of the strip 104 and adjusts the parameters thereof for adapting to the strip 104 (step 708).

The PoC device 102 may use a combination of impedance, voltage and current to inspect the strip 104. If the PoC device 102 determines that the strip 104 is not usable ("No" branch of step 710), the process 700 goes to step 702 and the PoC device 102 requests the user to replace the strip 104. Once the PoC device 102 determines that the strip 104 is workable ("Yes" branch of step 710), the PoC device 102 then requests the user to provide blood sample (step 712).

When receiving the blood sample, the PoC device 102 assesses the flow stability (step 714) and monitors the changes of current from the electrodes (step 716) as described above (also see FIGS. 24A and 24B). If the current is changing ("Yes" branch of step 718), the process 700 goes back to step 716 for further monitoring of current changes.

If the current changes stop ("No" branch of step 718), a timer is started to record interaction period of time (step 720) and the PoC device 102 begins to measure the impedance after a predefined interaction period of time expires (step 722). The PoC device 102 then compares the raw measurement to the calibration curve (step 724) and displays the results in terms of concentration (step 726). The quantitative or qualitative data is also uploaded to a server (step 730). The testing session then ends (step 732).

Figure 28:
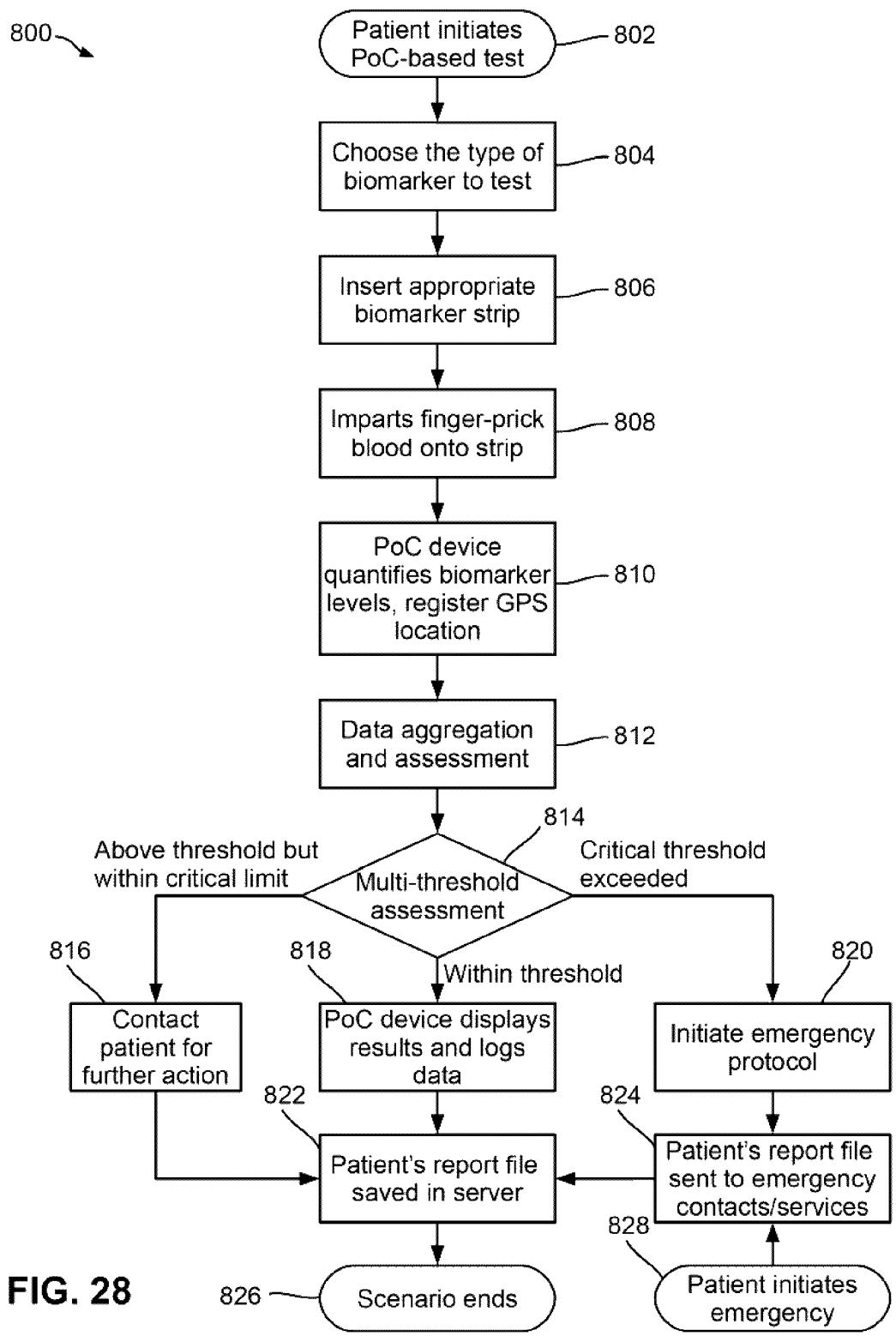
FIG. 28 is a flowchart showing a process for bodily fluid analysis, according to still some embodiments of this disclosure.

FIG. 28 is a flowchart showing a process 800 for bodily fluid analysis, according to some embodiments of this disclosure. The process 800 starts when a patient initiates a test using the PoC device 102 (step 802). The PoC device 102 is functionally coupled to a health-monitoring network system and in communication with a server as describe above.

Similar to the process 700, the user chooses the type of biomarker for test (step 804), inserts an appropriate biomarker strip 104 into the PoC device 102 (step 806), and imparts finger-prick blood sample onto the strip 104 (step 808). The PoC device 102 then quantifies the biomarker levels and registers the geolocation thereof using its GNSS components (e.g., its GPS component) (step 810). At step 812, the test and geolocation data is aggregated and assessed for obtaining an assessment of the user's health condition.

In these embodiments, the PoC device 102 comprises a plurality of thresholds for comparison with the test data, e.g., including a first threshold above which indicates an abnormal health condition and a second threshold above which indicates a critical health condition.

If at step 814, the PoC device 102 determines that the assessment of the user's health condition is above the first threshold but lower than the second threshold (i.e., abnormal but uncritical health condition), the PoC device 102 then communicates with the health-monitoring network system to allow the health-monitoring network system to contact the patient for further action (step 816). The process 800 then goes to step 822.

If at step 814, the PoC device 102 determines that the assessment of the user's health condition is below the first threshold (i.e., normal health condition), the PoC device 102 then displays the assessment of the user's health condition and logs the test data and the assessment of the user's health condition (step 818). The process 800 then goes to step 822.

If at step 814, the PoC device 102 determines that the assessment of the user's health condition is above the second threshold (i.e., critical health condition), the PoC device 102 then communicates with the health-monitoring network system to initiate an emergency protocol (step 820). The patient may also initiate an emergency via the PoC device 102 (step 828). The patient's report file (having, e.g., the user's history, biomarker data, geolocation, health condition assessment, and/or the like) is then sent to emergency contacts (such as the patient's doctor) and/or services (step 824). The process 800 then goes to step 822.

At step 822, the patient's report file is saved to the server of the health-monitoring network system. The process 800 ends (step 826).

As those skilled in the art will appreciate, the PoC device 102 disclosed herein may have various form factors such as being a hand-held device or a desktop device. The PoC device 102 may be used for monitoring suitable biomarkers or analytes originating from body fluid such as whole blood, plasma, serum, urine, and similar biological specimens, and providing physiologically relevant information. The physiologically relevant information may be securely transferred to healthcare practitioners, physicians, clinical and/or hospital management network including but not limited to public and/or private healthcare systems.

The PoC device 102 may be designed and implemented in a modular manner and comprise a plurality of detection modules for detecting different analytes. Each detection module may employ a specific technology to ascertain analyte concentration. The PoC device 102 may also comprise additional modules such as modules for initiating communication with external devices (e.g., mobile phones, hard drives, data centers, computer cloud, and/or the like).

Figure 29A:
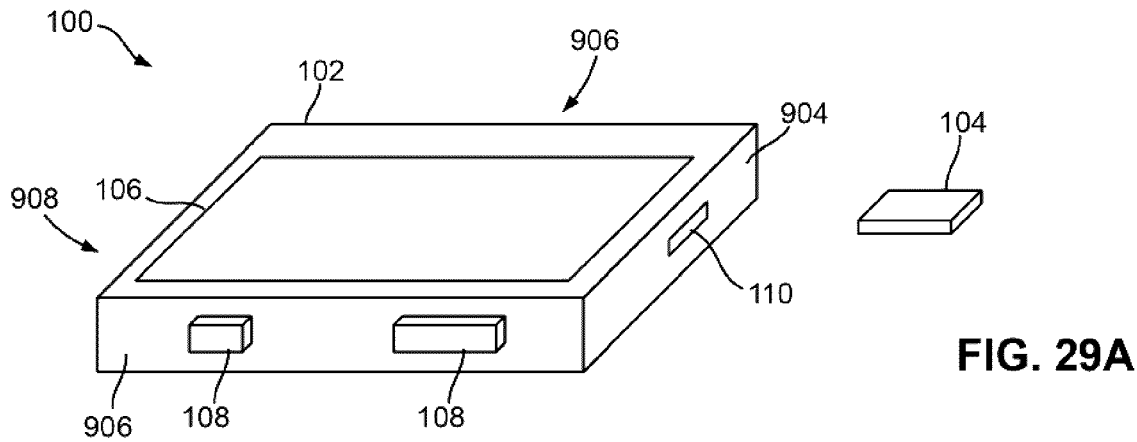
FIGS. 29A and 29B are schematic perspective and plan views, respectively, of a health monitoring system according to some embodiments of this disclosure.
Figure 29B:
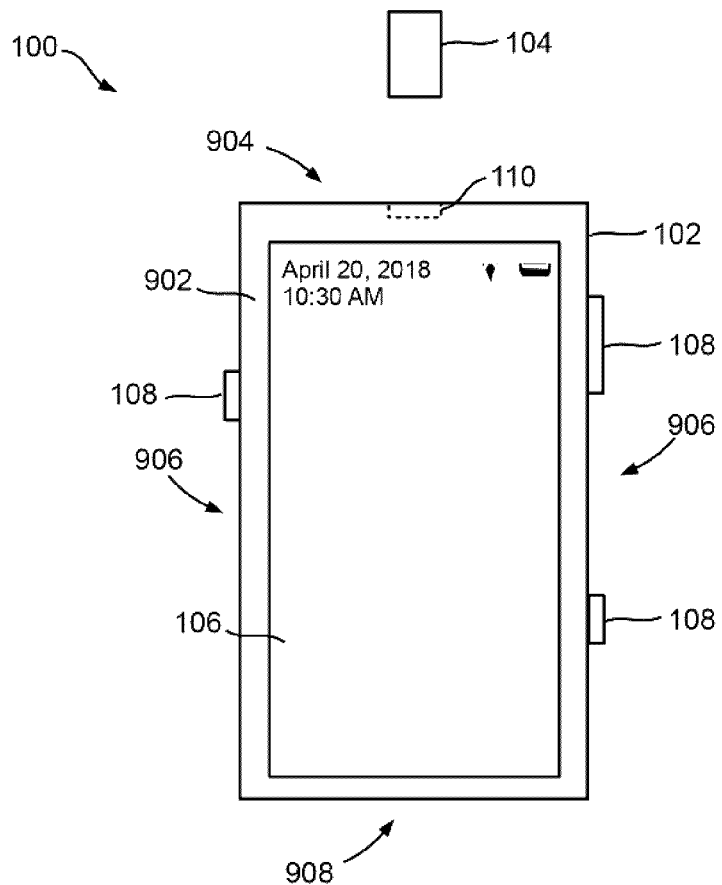

In above embodiments, the PoC device 102 comprises one or more buttons 108 beside the screen 106 for receiving user inputs. In some alternative embodiments as shown in FIGS. 29A and 29B, the PoC device 102 in these embodiments is similar to that shown in FIG. 1A. However, in these embodiments, the PoC device 102 may comprise a touchscreen 106 on a front wall 902 thereof, a strip-receiving port 110 on a top wall 904 thereof for receiving the strip 104, and one or more buttons 108 on the two opposite sidewalls 906 thereof. The buttons 108 may be used for receiving user inputs and performing various functions. For example, a first one of the buttons 108 may be used for activating the PoC device 102 or waking it up from a sleep mode, a second one of the buttons 108 may be used for starting a test, and a third one of the buttons 108 may be used for adjust the volume of a speaker integrated in the PoC device 102, when a user chooses to replay a test result via the speaker (e.g., when the PoC device is "reading" the test result). As those skilled in the art will appreciate, arranging the one or more buttons 108 on one or two sidewalls 906 of the PoC device 102 may facilitate a user to conveniently operate the PoC device 102 using one hand.

The strip-receiving port 110 may be preferably located at any suitable location of the PoC device 102 that would not interfere with the user's one-hand operation. For example, in some embodiments, the strip-receiving port 110 may be on a bottom wall 908 of the PoC device 102. In some other embodiments, the strip-receiving port 110 may be one of the sidewalls 906 of the PoC device 102.

In some embodiments wherein the PoC device 102 comprises a plurality of strip-receiving ports 110, the plurality of strip-receiving ports 110 may be preferably arranged on the PoC device 102 at any locations thereof that would not interfere with the user's one-hand operation.

In some embodiments, the PoC device 102 may comprise a USB port (e.g., a micro-USB port or a USB Type C port) or any suitable port for connecting to a power source for charging the battery of the PoC device 102.

In some embodiments, the PoC device 102 may comprise a connection port such as a USB port for receiving a strip adapter 252 similar to that shown in FIG. 13 but having a strip insert 254 with physical and electrical specifications suitable for inserting into the connection port. In these embodiments, the PoC device 102 may or may not comprise a strip-receiving port 110 depending on the implementation.

In the embodiments shown in FIG. 2, the PoC device 102 measures the resistance of the pair of identification electrodes 130 and 132 for identifying one or more biomarkers analyzable using the electrochemical-sensor structure 104 inserted therein. In some alternative embodiments, the electrochemical-sensor structure 104 comprises an identification circuitry with predefined electrical characteristics indicative of the one or more analyzable biomarkers.

Correspondingly, the PoC device 102 comprises a circuitry for coupling to the identification circuitry of the electrochemical-sensor structure 104 when the electrochemical-sensor structure 104 inserted therein is inserted therein, and determines the predefined electrical characteristics for identifying the one or more analyzable biomarkers.

For example, in some embodiments, the identification circuitry may be a circuitry with predefined capacitance indicative of the one or more analyzable biomarkers, and the PoC device 102 comprises a circuitry for determining the predefined capacitance for identifying the one or more analyzable biomarkers.

In some other embodiments, the identification circuitry may be a circuitry with predefined inductance indicative of the one or more analyzable biomarkers, and the PoC device 102 comprises a circuitry for determining the predefined inductance for identifying the one or more analyzable biomarkers.

In yet some other embodiments, the identification circuitry may be a circuitry storing a code indicative of the one or more analyzable biomarkers (e.g., an IC chip storing a code indicative of the one or more analyzable biomarkers), and the PoC device 102 comprises a reader circuitry for reading the code from the IC chip for determining the predefined inductance for identifying the one or more analyzable biomarkers.

In some of the above embodiments, the PoC device 102 uses an imaging component (such as a camera) for scanning an image (such as a one-dimensional barcode or a two-dimensional barcode) on the electrochemical-sensor structure 104 or on the carrying vial accommodating the electrochemical-sensor structures 104 for identifying the one or more analyzable biomarkers. Those skilled in the art will appreciate that, in some embodiments, other suitable images encoding the identities of the one or more analyzable biomarkers may also be used for identifying the one or more analyzable biomarkers as described above.

In some embodiments, the PoC device 102 may assess the flow stability and volume of fluid sample on the strip 104.

In some embodiments, the PoC device 102 may comprise one or more components for assisting in voltage and current signals to be read out or sent into the strip 104.

In some embodiments, the PoC device 102 may connect to a central server allowing a secured, two-way communication of information. The information may be calibration curve, test results, strip information, lot information, batch information, geospatial information, software information, and/or the like.

Although embodiments have been described above with reference to the accompanying drawings, those of skill in the art will appreciate that variations and modifications may be made without departing from the scope thereof as defined by the appended claims.

What is claimed is:

1. An apparatus for analyzing a bodily fluid sample of a user, the apparatus comprising:
a housing comprising at least one first port for receiving an electrochemical-sensor structure, the electrochemical-sensor structure comprising a first circuitry having a first set of electrodes for contacting the bodily fluid sample;
an identification circuitry for detecting predefined information stored with any of the electrochemical-sensor structure and a component associated with the electrochemical-sensor structure, the predefined information indicative of one or more biomarkers analyzable using the electrochemical-sensor structure;
an analysis circuitry comprising a set of coupling electrodes for electrically coupling to the first set of electrodes of the electrochemical-sensor structure for analyzing the identified one or more biomarkers in the bodily fluid sample;
a control circuitry coupled to the identification and analysis circuitries for determining a set of bio-sensing parameters based on the identified one or more biomarkers and for controlling the analysis circuitry to analyze the identified one or more biomarkers in the bodily fluid sample based on the set of bio-sensing parameters; and
an output for outputting an analytical result of said analysis of the identified one or more biomarkers in the bodily fluid sample;
wherein the set of coupling electrodes comprise at least a coupling reference electrode (RE), a coupling control electrode (CE), and a plurality of coupling working electrodes (Wes) for electrically coupling to a RE, a CE, and a plurality of WEs of the electrochemical-sensor structure;
wherein a first set of at least one of the coupling WEs are for electrically coupling to a first set of WEs of the electrochemical-sensor structure oversaturated with a first set of one or more capture ligands;
wherein a second set of at least one of the coupling WEs are for electrically coupling to a second set of WEs of the electrochemical-sensor structure cross-linked with predefined concentration of a second set of one or more capture ligands; and
wherein the analysis circuitry is for analyzing the identified one or more biomarkers in the bodily fluid sample by calculating analyte concentration based on the difference of the charge transfer resistances (RCTs) between the first and second sets of WEs of the electrochemical-sensor structure.

2. The apparatus of claim 1, wherein the predefined information comprises one or more of:
an impedance or resistance of a second circuitry of the electrochemical-sensor structure indicative of the one or more biomarkers;
data stored in a radio frequency identification (RFID) tag indicative of the one or more biomarkers; and
an image indicative of the one or more biomarkers.

3. The apparatus of claim 1, wherein the analysis circuitry is configured for measuring one or more impedances, one or more currents, and/or one or more voltages of the first circuitry for analyzing the identified one or more biomarkers in the bodily fluid sample.

4. The apparatus of claim 1, wherein the analysis circuitry comprises at least one potentiostat circuitry for electrically coupling to the first circuitry for analyzing the identified one or more biomarkers in the bodily fluid sample.

5. The apparatus of claim 1, wherein the analysis circuitry is for analyzing the identified one or more biomarkers in the bodily fluid sample by calculating analyte concentration based on the difference of the charge transfer resistances (RCTs) between the first and second sets of WEs of the electrochemical-sensor structure and using a statistical method.

6. The apparatus of claim 1 further comprising:
an adaptor for electrically removably coupling to the apparatus, said adaptor comprising a plurality of second ports for receiving a plurality of additional electrochemical-sensor structures.

7. The apparatus of claim 1, further comprising:
a third port for physically and electrically coupling to a smartphone.

8. The apparatus of claim 1, wherein the analysis circuitry and/or the control circuitry comprise an electrochemical module for detecting and analyzing N-terminal Pro B-type natriuretic peptide (NT-pro-BNP), a fluorescence module and a polymerase chain reaction (PCR) module for detecting and analyzing aptamer-based ligand, and an absorbance module for metabolite analysis.

9. The apparatus of claim 8, wherein the analysis circuitry and/or the control circuitry further comprise a memory storing therein a calibration curve for determining concentration of the identified one or more biomarkers.

10. The apparatus of claim 1, further comprising:
one or more global navigation satellite system (GNSS) components for obtaining geospatial information of the apparatus; and
wherein the output is for outputting the analytical result and the geospatial information.

11. An electrochemical-sensor structure comprising:
a substrate;
a first circuitry comprising a first set of electrodes distributed on the substrate and extending into a sampling region of the substrate for contacting a bodily fluid sample; and
an identification structure comprising predefined information indicative of one or more biomarkers of the bodily fluid sample analyzable using the electrochemical-sensor structure;
wherein the first set of electrodes comprise at least a reference electrode (RE), a control electrode (CE), and a plurality of working electrodes (WEs); and wherein a first set of at least one of the WEs are oversaturated with a first set of one or more capture ligands and a second set of at least one of the WEs are cross-linked with predefined concentration of a second set of one or more capture ligands.

12. The electrochemical-sensor structure of claim 11, wherein the substrate is a track-etched membrane having a porosity equal to or greater than 30%.

13. The electrochemical-sensor structure of claim 11, wherein the substrate comprises a Poly(methyl methacrylate) (PMMA) membrane.

14. The electrochemical-sensor structure of claim 11, wherein the identification structure comprises one or more of:
   a second circuitry having a predefined impedance indicative of the one or more biomarkers;
   a radio frequency identification (RFID) tag storing data indicative of the one or more biomarkers; and
   an image indicative of the one or more biomarkers.

15. The electrochemical-sensor structure of claim 11, wherein the CE extends along at least two edges of the sampling region thereby encircling the rest of the first set of electrodes.

16. The electrochemical-sensor structure of claim 11, wherein the sampling region of the substrate comprises:
   one or more introductory channels about an edge thereof for introducing the bodily fluid sample using the capillary effects;
   a heterophile plasma separating component (HF-PSC) unit adjacent the one or more introductory channels for receiving the bodily fluid sample therefrom and filtering out interfering components of the bodily fluid sample; and
   an analyte-drop chamber intermediate the HF-PSC and the first set of electrodes, the analyte-drop chamber receiving the filtered bodily fluid sample from the HF-PSC for allowing the filtered bodily fluid sample to contact the first set of electrodes.

17. The electrochemical-sensor structure of claim 16, wherein at least one of the one or more introductory channels is of a funnel shape and comprises an opening adjacent the edge of the sampling region and tapering towards the HF-PSC unit.

18. The electrochemical-sensor structure of claim 16, wherein at least one of the one or more introductory channels is engraved on the substrate or formed by a gap in a coating on the substrate.

19. The electrochemical-sensor structure of claim 16, wherein the HF-PSC unit comprises symmetrical and/or asymmetrical pores with varied pore sizes.

20. The electrochemical-sensor structure of claim 16 further comprising:
   one or more capillary channels each comprising an entrance in or about the analyte-drop chamber and extending from the analyte-drop chamber to the first set of electrodes;
   wherein at least one of the one or more capillary channels is hydrophilic to the bodily fluid sample and comprises an abrupt expansion at a distance to the entrance, for controlling a volume of the bodily fluid sample therein; and
   wherein at least one WE extends to the at least one of the one or more capillary channels at a location intermediate the entrance and the expansion thereof for interacting with the bodily fluid sample therein.

21. The electrochemical-sensor structure of claim 16 further comprising:
   one or more capillary channels each comprising an entrance in or about the analyte-drop chamber and extending from the analyte-drop chamber to the first set of electrodes;
   wherein at least one of the one or more capillary channels is hydrophobic to the bodily fluid sample and comprises an abrupt tapering portion at a distance to the entrance, for controlling a volume of the bodily fluid therein; and
   wherein at least one WE extends to the at least one of the one or more capillary channels at a location intermediate the entrance and the tapering portion thereof for interacting with the bodily fluid sample therein.

22. A system for analyzing a bodily fluid sample of a user, the system comprising:
   an electrochemical-sensor structure for receiving thereon the bodily fluid sample; and
   a testing apparatus collaborating with the electrochemical-sensor structure for analyzing the bodily fluid sample;
   wherein the electrochemical-sensor structure comprises:
   a substrate,
   a first circuitry comprising a first set of electrodes distributed on the substrate and extending into a sampling region of the substrate for contacting a bodily fluid sample, and
   an identification structure comprising predefined information indicative of one or more biomarkers of the bodily fluid sample analyzable using the electrochemical-sensor structure;
   wherein the first set of electrodes comprise at least a reference electrode (RE), a control electrode (CE), and a plurality of working electrodes (WEs); and wherein a first set of at least one of the WEs are oversaturated with a first set of one or more capture ligands and a second set of at least one of the WEs are cross-linked with predefined concentration of a second set of one or more capture ligands; and
   wherein the testing apparatus comprises:
      a housing comprising at least one first port for receiving the electrochemical-sensor structure, the electrochemical-sensor structure comprising a first circuitry having a first set of electrodes for contacting the bodily fluid sample,
      an identification circuitry for detecting the predefined information of the identification structure of the electrochemical-sensor structure for determining the one or more biomarkers analyzable using the electrochemical-sensor structure,
      an analysis circuitry comprising a set of coupling electrodes for electrically coupling to the first set of electrodes of the electrochemical-sensor structure for analyzing the identified one or more biomarkers in the bodily fluid sample,
      a control circuitry coupled to the identification and analysis circuitries for determining a set of bio-sensing parameters based on the identified one or more biomarkers and for controlling the analysis circuitry to analyze the identified one or more biomarkers in the bodily fluid sample based on the set of bio-sensing parameters, and
   an output for outputting an analytical result of said analysis of the identified one or more biomarkers in the bodily fluid sample.

* * * * *

UNITED STATES PATENT AND TRADEMARK OFFICE
CERTIFICATE OF CORRECTION

| | | |
|---|---|---|
| PATENT NO. | : 12,117,435 B2 | Page 1 of 1 |
| APPLICATION NO. | : 17/261476 | |
| DATED | : October 15, 2024 | |
| INVENTOR(S) | : Raman Koul et al. | |

It is certified that error appears in the above-identified patent and that said Letters Patent is hereby corrected as shown below:

On the Title Page

Item (72) Inventors, delete "Gang Wang" and replace with -- Gang (A.K.A. Joseph) Wang --

Signed and Sealed this
Twenty-sixth Day of November, 2024

Katherine Kelly Vidal
*Director of the United States Patent and Trademark Office*